(12) United States Patent
Caspi et al.

(10) Patent No.: US 7,972,779 B2
(45) Date of Patent: Jul. 5, 2011

(54) METHOD FOR ASSESSING PREDISPOSITION TO DEPRESSION

(75) Inventors: Avshalom Caspi, London (GB); Terrie E. Moffitt, London (GB)

(73) Assignee: Wisconsin Alumni Research Foundation, Madison, WI (US)

( * ) Notice: Subject to any disclaimer, the term of this patent is extended or adjusted under 35 U.S.C. 154(b) by 687 days.

(21) Appl. No.: 10/889,450

(22) Filed: Jul. 12, 2004

(65) Prior Publication Data

US 2005/0037405 A1     Feb. 17, 2005

Related U.S. Application Data

(60) Provisional application No. 60/486,640, filed on Jul. 11, 2003.

(51) Int. Cl.
*C12Q 1/68* (2006.01)
*C12P 19/34* (2006.01)
*C07H 21/02* (2006.01)
*C07H 21/04* (2006.01)

(52) U.S. Cl. ........ 435/6; 435/91.2; 536/24.1; 536/24.33

(58) Field of Classification Search .................. None
See application file for complete search history.

(56) References Cited

FOREIGN PATENT DOCUMENTS
CA    2 344 093    8/2002

OTHER PUBLICATIONS

Caspi et al. Science. Aug. 2002. 297: 851-854.*
Gelernter et al. Human Genetics. 1997. 101: 243-246.*
Wang et al. PLoS biology. 2007. 5: 0335-0342.*
Surtees et al. Biological Psychiatry. 2006. 59: 224-229.*
Gillespie et al. Psychological Medicine. 2005. 35: 101-111.*
Lucentini. The Scientist. Dec. 2004, p. 20.*
Chipman et al. American Journal of Medical Genetics. 2007. 144B: 561-565.*
Chorbov et al. American Journal of Medical Genetics. 2007. 144B. 830-833.*
Taylor et al Biol Psychiatry. 2006. 60: 671-676.*
Risch et al. JAMA. Jun. 17, 2009. 301(23): 2462-2471.*
Munafo et al. Biol Pyschiatry. 2009. 65 : 211-219.*
Mental Health: A Report of the Surgeon General, Chapter 4 "Stressful Life Events," available via url: <surgeongeneral.gov/library/mentalhealth/chapter4/sec1_1.html>, printed on Mar. 21, 2011.*
Bennett, A.J., et al. "Early Experience and Serotonin Transporter Gene Variation Interact to Influence Primate CNS Function," Molecular Psychiatry, vol. 7, No. 1, pp. 118-122 (2002).
Champoux, M., et al. "Serotonin Transporter GEne Polymorphism, Differential Early Rearing, and Behavior in Rhesus Monkey Neonates," Molecular Psychiatry, vol. 7, No. 10, pp. 1058-1063 (2002).
Hu X., et al. "Genotyping of the HTTLPR Ins/Del by dHPLC followed by Association/Linkage Disequilibrium to Behavior in a Southwest American Indian Isolate," American Journal of Human Genetics, vol. 7, No. 2, pp. 213-216 (2002).

Lesch, K.P., et al. "The 5-HT Transporter Gene-Linked Polymorphic Region (5-HTTLPR) in Evolutionary Perspective: Alternative Biallelic Variation in Rhesus Monkeys" Journal of Neural Transmission vol. 104 No. 11-12 pp. 1259-1266 (1997).
Lesch, K.P. "Molecular Foundation of Anxiety Disorders," Journal of Neural Transmission, vol. 108, No. 6, pp. 717-746 (2001).
Moreno, F.A. "Association Between a Serotonin Transporter Promoter REgion Ploymorphism and Mood Response During Tryptophan Depletion," Molecular Psychiatry, vol. 7, No. 2, pp. 213-216 (2002).
Rosenthal, N.E., et al. "Role of Serotonin Transporter Promoter Repeat Length Polymorphism (5-HTTLPR) in Seasonality and Seasonal Affective Disorder," Molecular Psychiatry vol 3 No. 2 pp. 175-177 (1998).
Veenstra-Vanderweele, J., et al. "Pharmacogenetics and the Serotonin System: Initial Studies and Future Directions," European Journal of Pharmacology, vol. 410, No. 2-3, pp. 165-181 (2000).
Cervilla J, et al., "The risk for depression conferred by stressful life events is modified by variation at the serotonin transporter 5HTTLPR genotype: evidence from the Spanish Predict-Gene cohort," Mol. Psychiatry 12:748-755 (2007).
Covault J, et al., "Interactive effects of the serotonin transporter 5-HTTLPR polymorphism and stressful life events on college student drinking and drug use," Biol. Psychiatry 61:609-616 (2007).
Dick D, et al., "Association analyses of the serotonin transporter gene with lifetime depression and alcohol dependence in the collaborative study on the genetics of alcoholism (COGA) sample," Psychiatr. Genet. 17:35-38 (2007).
Eley T, et al., "Gene-environment interaction analysis of serotonin system markers with adolescent depression," Mol. Psychiatry 9:908-915 (2004).
Fox N, et al., "Evidence for a gene-environment interaction in predicting behavioral inhibition in middle childhood," Psychol. Sci. 16:921-926 (2005).
Grabe H, et al., "Mental and physical distress is modulated by a polymorphism in the 5-HT transporter gene interacting with social stressors and chronic disease burden," Mol. Psychiatry 10:220-224 (2005). Gibb B, et al., "Serotonin transporter (5-HTTLPR) genotype, childhood abuse, and suicide attempts among adult psychiatric inpatients," Suicide Life Threat. Behav. 36:687-693 (2006).
Jacobs N, et al., "Stress-related negative affectivity and genetically altered serotonin transporter function," Arch. Gen. Psychiatry 63:989-996 (2006).
Kaufman J, et al., "Brain-Derived Neurotrophic Factor—5-HTTLPR Gene Interactions and Environmental Modifiers of Depression in children," Biol. Psychiatry 59:673-680 (2006).
Kaufman J, et al., "Social supports and serotonin transporter gene moderate depression in maltreated children," PNAS 101:17316-17321 (2004).
Kendler K, et al., "The interaction of stressful life events and a serotonin transporter polymorphism in the prediction of episodes of major depression: a replication," Arch. Gen. Psychiatry 62:529-535 (2005).
Kim J, et al., "Interactions between life stressors and susceptibility genes (5-HTTLPR and BDNF) on depression in Korean elders," Biol. Psychiatry 62:423-528 (2007).

(Continued)

*Primary Examiner* — Carla Myers
(74) *Attorney, Agent, or Firm* — Quarles & Brady LLP

(57) ABSTRACT

The present invention relates to diagnostic methods for assessing predisposition of a subject to a mental disorder phenotype having an association with an at-risk allele of a brain-functional gene having a plurality of alleles, the association being conditioned by a pathogenic environmental risk factor status condition. Additionally, the invention relates to methods for discovering a conditional association between a mental disorder phenotype and an at-risk allele of a brain-functional gene having a plurality of alleles, the association being conditioned by a pathogenic environmental risk factor status condition.

6 Claims, 5 Drawing Sheets

OTHER PUBLICATIONS

Lenze E, et al., "Association of the serotonin transporter gene-linked polymorphic region (5-HTTLPR) genotype with depression in elderly persons after hip fracture," Am. J. Geriatr. Psychiatry 13:428-432 (2005).

Mandelli L, et al., "Interaction between serotonin transporter gene, catechol-O-methyltransferase gene and stressful life events in mood disorders," Int. J. Neuropsychopharmacol. 10:437-447 (2007).

Nakatani D, et al., "Influence of serotonin transporter gene polymorphism on depressive symptoms and new cardiac events after acute myocardial infarction," Am. Heart J. 150:652-658 (2005).

Roy A, et al., "Interaction between childhood trauma and serotonin transporter gene variation in suicide attempts," Neuropsychopharmacology 32:2046-2052 (2007).

Scheid J, et al., "Depressive symptoms in mid-pregnancy, lifetime stressors and the 5-HTTLPR genotype," Genes Brain Behav. 6:453-464 (2007).

Stein M, et al., "Gene-by-environment (serotonin transporter and childhood maltreatment) interaction for anxiety sensitivity, an intermediate phenotype for anxiety disorders," Neuropsychopharmacology [epub ahead of print on Apr. 25, 2007].

Taylor S, et al., "Early family environment, current adversity, the serotonin transporter promoter polymorphism, and depressive symptomatology," Biol. Psychiatry 60:671-676 (2006).

Wilhelm K, et al., "Life events, first depression onset and the serotonin transporter gene," Br. J. Psychiatry, 188:210-215 (2006).

Zalsman G, et al., "Association of a triallelic serotonin transporter gene promoter region (5-HTTLPR) polymorphism with stressful life events and severity of depression," Am. J. Psychiatry, 163:1588-1593 (2006).

Andrews, G., Antstey, K., Brodaty, H. et al. (1999). Recall of depressive episodes, 25 years previously. Psychol Med 29: 787-791.

Andrews G., Poulton R., Skoog I. (2005). Lifetime risk for depression: Restricted to a minority or waiting for most? Brit J. Psychiatr 187: 495-496.

Ansorge, M. S., Zhou, M., Lira, A., Hen, R., Gingrich, J. A. (2004). Early-life blockade of the 5-HT transporter alters emotional behavior in adult mice. Science, 306, 879-881.

Araya, Ricardo, Jon Heron, Mary-Anne Enoch, Jonathan Evans, Glyn Lewis, David Nutt, David Goldman, (2008). Effects of stressful life events, maternal depression and 5-HTTLPR genotype on emotional symptoms in pre-adolescent children. American Journal of Medical Genetics Part B: Neuropsychiatric Genetics, 9999(9999), n/a.

Barr, C. S., Newman, T. K., Shannon, C., Parker, C., Dvoskin, R. L., Becker, M. L., Schwandt, M., Champoux, M., Lesch, K. P., Goldman, D., Suomi, S. J., Higley, J. D. (2004). Rearing condition and rh5-HTTLPR interact to influence limbic-hypothalamic-pituitary-adrenal axis response to stress in infant macaques. Biological Psychiatry, 55, 733-738.

Barry, R. A., Kochanska, G., & Philibert, R. A. (2008). G x E interaction in the organization of attachment: mothers' responsiveness as a moderator of children's genotypes. Journal of Child Psychology and Psychiatry, 49(12), 1313-1320.

Barton, D.A. et al. (2008). Elevated brain serotonin turnover in patients with depression: Effect of genotype and therapy. Archives of General Psychiatry, 65, 38-46.

Battaglia, M., Ogliari, A., Zanoni, A., Citterio, A., Pozzoli, U., Giorda, R., Maffei, C., Marino, C. (2005). Influence of the serotonin transporter promoter gene and shyness on children's cerebral responses to facial expressions. Archives of General Psychiatry, 62, 85-94.

Beevers, C. G., Gibb, B. E., McGeary, J. E., Miller, I. W. (2007). Serotonin transporter genetic variation and biased attention for emotional word stimuli among psychiatric inpatients. Journal of Abnormal Psychiatry, 116, 208-212.

Brody, GH, Beach, SRH, Philibart, RA, Chen, Y, Lei, M, Murry, VM, Brown, AC (2009). Parenting moderates a genetic vulnerability factor in longitudinal increase in youth's substance use. J of Consulting and Clinical Psychology, 77, 1-11.

Brown, G. W., & Harris, T. O. (2008). Depression and the serotonin transporter 5-HTTLPR polymorphism: A review and a hypothesis concerning gene-environment interaction. Journal of Affective Disorders, 111(1), 1-12.

Brummett, B. H., Krystal, A. D., Ashley-Koch, A., Kuhn, C. M., Zuchner, S., Siegler, I. C., Barefoot, J. C., Ballard, E. L., Gwyther, L. P., Williams, R. B. (2007). Sleep quality varies as a function of 5-HTTLPR genotype and stress.

Canli, T. & Lesch, K-P. (2007). Long story short : The serotonin transporter in emotion regulation and social cognition. Nature Neuroscience, 10, 1103-1109.

Canli, T., Qiu, M., Omura, K., Congdon, E., Haas, B. W., Amin, Z., Herrmann, M. J., Constable, R. T., Lesch, K. P. (2006). Neural correlates of epigenesis. PNAS, 24, 16033-16038.

Carola, V., Frazzetto, G., Pascucci, T., Audero, E., Puglisi-Allegra, S., Cabib, S., et al. (2007). Identifying molecular substrates in a mouse model of the serotonin transporter x environment risk factor for anxiety and depression. Biological psychiatry, 63(9), 840-846.

Cicchetti, D., Rogosch, F. A., & Sturge-Apple, M. L. (2007). Interactions of child maltreatment and serotonin transporter and monoamine oxidase A polymorphisms: Depressive symptornatology among adolescents from low socioeconomic status backgrounds. Development and Psychopathology, 19(4), 1161-1180.

Cyran, J. F. & Holmes, A. (2005). Model organisms: The ascent of mouse: advances in modeling human depression and anxiety. Nature Reviews Drug Discovery, 4, 775-790.

Fallgatter, A. J., Herrmann, M. J., Roemmler, J., Ehlis, A-C., Wagener, A., Heidrich, A., Ortega, G., Zeng, Y., Lesch, K-P. (2004). Allelic variation of serotonin transporter function modulates the brain electrical response for error processing. Neuropsychopharmacology, 29, 1506-1511.

Gotlib, I. H., Joormann, J., Minor, K. L., & Hallmayer, J. (2008). HPA Axis Reactivity: A Mechanism Underlying the Associations Among 5-HTTLPR, Stress, and Depression. Biological psychiatry, 63(9), 847-851.

Gunthert, K. C., Conner, T. S., Armeli, S., Tennen, H., Covault, J., Kranzler, H. R. (2007). Serotonin transporter gene polymorphism (5-HTTLPR) and anxiety reactivity in daily life: A daily process approach to gene-environment interaction. Psychosomatic Medicine, 69, 762-768.

Hariri, A. R. & Holmes, A. (2006). Genetics of emotional regulation: the role of the serotonin transporter in neural function. Trends in Cognitive Sciences, 10, 182-191.

Hariri, A. R., Drabant, E. M., Munoz, K. E., Kolachana, B. S., Mattay, V. S., Egan, M. F., Weinberger, D. R. (2005). A susceptibility gene for affective disorders and the response of the human amygdala. Archives of General Psychiatry, 62, 146-152.

Hariri, A. R., Drabant, E. M., Weinberger, D. R. (2006). Imaging genetics: Perspectives from studies of genetically driven variation in serotonin function and corticolimbic affective processing. Biological Psychiatry, 59, 888-897.

Hariri, A. R., Mattay, V. S., Tessitore, A., Kolachana, B., Fera, F., Goldman, D., Egan, M. F., Weinberger, D. R. (2002). Serotonin transporter genetic variation and the response of the human amygdale. Science, 297, 400-403.

Heinz, A., Braus, D. F., Smolka, M. N., Wrase, J., Puls, I., Hermann, D., Klein, S., Grusser, S. M., Flor, H., Schumann, G., Mann, K., Buchel, C. (2005). Amygdala-prefrontal coupling depends on a genetic variation of the serotonin transporter. Nature Neuroscience, 8, 20-21.

Holmes, A., Murphy, D. L., Crawley, J. N. (2003). Abnormal behavioral phenotypes of serotonin transporter knockout mice: Parallels with human anxiety and depression. Biological Psychiatry, 54, 953-959.

Horwitz, A. V. (2005). Media portrayals and health inequalities: A case study of characterizations of Gene x Environment interactions.

Kalin, N. H., Shelton, S. E., Fox, A. S., Rogers, J., Oakes, T. R., & Davidson, R. J. (2008). The serotonin transporter genotype is associated with intermediate brain phenotypes that depend on the context of eliciting stressor. Molecular Psychiatry, 13(11), 1021-1027.

Kaufman, J., Yang, B. Z., Douglas-Palumberi, H., Crouse-Artus, M., Lipshitz, D., Krystal, J. H., Gelernter, J. (2007). Genetic and environmental predictors of early alcohol use. Biological Psychiatry, 61, 1228-1234.

Kilpatrick, D. G., Koenen, K., Ruggiero, K. J., Acierno, R., Galea, S., Resnick, H., Roitzsch, J., Boyle, J., Gelernter, J. (2007). Do serotonin transporter gene and social support moderate posttraumatic stress disorder and depression in hurricane-exposed adults? American J of Psychiatry, 164, 1693-1699.

Kohen, R., Cain, K. C., Mitchell, P. H., Becker, K., Buzaitis, A., Millard, S. P., et al. (2008). Association of Serotonin Transporter Gene Polymorphisms With Poststroke Depression. Archives of General Psychiatry, 65(11), 1296-1302.

Kruijshaar ME, Barendrecht J., Vos T., de Graaf R., Spijker J., Andrews G., (2005). Lifetime prevalence estimates of major depression: An indirect estimation method and a quantification of recall bias. Eur J Epidemiol, 20:103-111.

Lazary, J., Aron, L., Xenia, G., Anita, B., Eszter, M., Gabriella, J., et al. (2008). New Evidence for the Association of the Serotonin Transporter Gene (SLC6A4) Haplotypes, Threatening Life Events, and Depressive Phenotype. Biological psychiatry, 64(6), 498-504.

Leonardo, E. D. & Hen, R. (2006). Genetics of affective and anxiety disorders. Annual Review of Psychology, 57, 117-137.

Lonsdorf, TB, Weuke, Al, Nikamo, P, Schalling, M, Hamm, AO, and Ohman, A. (2009). Genetic gating of human fear learning and extinction. Possible implications for gene-environment interaction in anxiety disorder. Psychological science, e-pub ahead of print.

Monroe, S. M., & Reid, M. W. (2008). Gene-Environment Interactions in Depression Research: Genetic Polymorphisms and Life-Stress Polyprocedures. Psychological Science, 19(10), 947-956.

Munafò, M. R., Durrant, C., Lewis, G., & Flint, J. (2009). Gene x Environment Interactions at the Serotonin Transporter Locus. Biological psychiatry, 65(3), 211-219.

Murphy, D. L., Li, Q., Engel, S., Wichems, C., Andrews, A., Lesch, K. P., Uhl, G. (2001). Genetic perspectives on the serotonin transporter. Brain Research Bulletin, 56, 487-494.

Nelson, E. E., & Winslow, J. T. (2008). Non-Human Primates: Model Animals for Developmental Psychopathology. Neuropsychopharmacology, 34(1), 90-105.

Nobile, M. , Monica Bellina, Cecilia Marino, Roberto Giorda, Ombretta Carlet, Laura Vanzin, Massimo Molteni, Marco Battaglia, (2008). The influence of family structure, the TPH2; G-703T and the 5-HTTLPR serotonergic genes upon affective problems in children aged 10 &14 years. Journal of Child Psychology and Psychiatry, 9999(9999).

Otte, C., McCaffery, J., Ali, S., Whooley, M. A. (2007). Association of a serotonin transporter polymorphism (5-HTTLPR) with depression, perceived stress, and norepinephrine in patients with coronary disease: The heart and soul study. American Journal of Psychiatry, 164, 1379-1384.

Patten, SB., (2003). Recall bias and major depression lifetime prevalence. Soc Psychiatry Psychiatr Epidemiol, 38, 290-296.

Pezawas, L., Meyer-Lindenberg, A., Drabant, E. M., Verchinski, B. A., Munoz, K. E., Kolachana, B. S., Egan, M. F., Mattay, V. S., Hariri, A. R., Weinberger. (2005). 5-HTTLPR polymorphism impacts human cingulated-amygdala interactions: a genetic susceptibility mechanism for depression. Nature Neuroscience, 8, 828-834.

Power, T., Stewart, R., Ancelin, M.-L., Jaussent, I., Malafosse, A., & Ritchie, K. 5-HTTLPR genotype, stressful life events and late-life depression: No evidence of interaction in a French population. Neurobiology of Aging, In Press, Corrected Proof.

Sjoberg, R. L., Nilsson, K. W., Nordquist, N., Ahrvik, J., Leppert, J., Lindstram, L., et al. (2006). Development of depression: Sex and the interaction between environment and a promoter polymorphism of the serotonin transporter gene. International Journal of Neuropsychopharmacology, 9(4), 443-449.

Steiger, H., Richardson, J., Joober, R., Gauvin, L., Israel, M., Bruce, K. P., Nmk, N. Y. K., Young, S. (2007). The 5HTTLPR polymorphism, prior maltreatment, and dramatic-erratic personality manifestations in women with bulimic syndromes. Journal of Psychiatry and Neuroscience, 32, 354-362.

Surtees, P. G., Wainwright, N. W., Willis-Owen, S. A., Luben, R., Day, N. E., Flint, J. (2006). Social adversity, the serotonin transporter (5-HTTLPR), polymorphism and major depressive disorder. Biological Psychiatry, 59, 224-229.

Uher, R. & McGuffin, P. (2007). The moderation by the serotonin transporter gene of environmental adversity in the aetiology of mental illness: Review and methodological analysis. Molecular Psychiatry [epub ahead of print].

Uher, R. (2008). The implications of gene-environment interactions in depression: will cause inform cure? Molecular Psychiatry, 13(12), 1070-1078.

Watson, K. K., Ghodasra, J. H., & Platt, M. L. (2009). Serotonin Transporter Genotype Modulates Social Reward and Punishment in Rhesus Macaques. PLoS ONE, 4(1), e4156.

Wellman, C. L., Izquierdo, A., Garrett, J. E., Martin, K. P., Carroll, J., Millstein, R., Lesch, K-P., Murphy, D. L., Holmes, A. (2007). Impaired stress-coping and fear extinction and abnormal corticolimbic morphology in serotonin transporter knock-out mice. Journal of Neuroscience, 27, 684-691.

Wilhelm, K., Siegel, J. E., Finch, A. W., Hadzi-Pavlovic, D., Mitchell, P. B., Parker, G., Schofield, P. R. (2007). The long and the short of it: Associations between 5-HTT genotypes and coping with stress. Psychosomatic Medicine, 69, 614-620.

Xie, P. et al. (in review) The Interactive Effect of Stressful Life Events and Serotonin Transporter 5-2 HTTLPR Genotype on PTSD Diagnosis In Two Independent Populations.

Zammit, S. & Owen, M. J. (2006). Stressful life events, 5-HTT genotype and risk of depression. British Journal of Psychiatry, 188, 199-201.

Anguelova M, Benkelfat C, Turecki G. A systematic review of association studies investigating genes coding for serotonin receptors and the serotonin transporter, II: suicidal behavior. Mol. Psychiatry. 2003; 8(7):646-653.

Levinson DF. The genetics of depression: a review. Biol. Psychiatry. 2006; 60(2):84-92.

Middeldorp CM, Cath DC, Beem AL, Willemsen G, Boomsma DI. Life events, anxious depression and personality: a prospective and genetic study. Psychol. Med. 2008; 38(11):1557-1565.

Middeldorp CM, de Geus EJ, Beem AL, et al. Family based association analyses between the serotonin transporter gene polymorphism (5-HTTLPR) and neuroticism, anxiety and depression. Behav. Genet. 2007; 37(2):294-301.

Laucht M, Treutlein J, Blomeyer D, et al. Interaction between the 5-HTTLPR serotonin transporter polymorphism and environmental adversity for mood and anxiety psychopathology: evidence from a high-risk community sample of young adults [published online ahead of print Jan. 20, 2009]. Int. J. Neuropsychopharmacol. 2009; 1-11. doi:10.1017/S1461145708009875.

Aguilera M, Arias B, Wichers M, et al. Early adversity and 5-HTT/BDNF genes: new evidence of geneenvironment interactions on depressive symptoms in a general population [published online ahead of print Feb. 12, 2009]. Psychol. Med. 2009:1-8. doi: 10.1017/S0033291709005248.

Brummett BH, Boyle SH, Siegler IC, et al. Effects of environmental stress and gender on associations among symptoms of depression and the serotonin transporter gene linked polymorphic region (5-HTTLPR). Behay. Genet. 2008; 38(1):34-43.

Katsuyama H, Tomita M, Hidaka K, et al. Association between serotonin transporter gene polymorphisms and depressed mood caused by job stress in Japanese workers. Int. J. Mol. Med. 2008; 21(4): 499-505.

Veletza S, Samakouri M, Emmanouil G, Trypsianis G, Kourmouli N, Livaditis M. Psychological vulnerability differences in students—carriers or not of the serotonin transporter promoter allele S: effect of adverse experiences. Synapse. 2009; 63(3):193- 200.

Wichers M, Kenis G, Jacobs N, et al. The BDNF Val(66)Met x 5-HTTLPR x child adversity interaction and depressive symptoms: an attempt at replication. Am. J. Med. Genet. B. Neuropsychiatr. Genet. 2008; 147B(1):120-123.

Zhang K, Xu Q, Xu Y, et al. The combined effects of the 5-HTTLPR and 5-HTR1A genes modulates the relationship between negative life events and major depressive disorder in a Chinese population. J. Affect. Disord. 2009; 114 (1-3):224-231.

Brugha T, Bebbington P, Tennant C, Hurry J. The List of Threatening Experiences: a subset of 12 life event categories with considerable long-term contextual threat. Psychol. Med. 1985; 15(1):189-194.

Brugha TS, Cragg D. The List of Threatening Experiences: the reliability and validity of a brief life events questionnaire. Acta Psychiatr. Scand. 1990; 82(1): 77-81.

Eaton WW. Life events, social supports, and psychiatric symptoms: a re-analysis of the New Haven data. J. Health. Soc. Behav. 1978; 19(2):230-234.

Eaves LJ. Genotype x environment interaction in psychopathology: fact or artifact? Twin. Res. Hum. Genet. 2006; 9 (1):1-8.

Joober R, Sengupta S, Schmitz N. Serotonin transporter, stressful life events, and depression severity. Am. J. Psychiatry. 2007; 164(5):829-830, author reply 830-831.

Wray NR, Coventry WL, James MR, Montgomery GW, Eaves LJ, Martin NG. Use of monozygotictwins to investigate the relationship between 5HTTLPR genotype, depression and stressful life events: an application of Item Response Theory. Novartis Found. Symp. 2008; 293:48-59, discussion 59-70.

Brummett BH, Muller CL, Collins AL, et al. 5-HTTLPR and gender moderate changes in negative affect responses to tryptophan infusion. Behav. Genet. 2008; 38(5):476-483.

Ottman R. Gene-environment interaction: definitions and study designs. Prev. Med. 1996; 25(6): 764-770.

Mather K, Jinks J. Biometrical Genetics: The Study of Continuous Variation. London, England: Chapman & Hall; 1982.

Guo G, Tong Y, Xie CW, Lange LA. Dopamine transporter, gender, and number of sexual partners among young adults. Eur. J. Hum. Genet. 2007; 15(3):279-287.

Guo G, Roettger ME, Shih JC. Contributions of the DAT1 and DRD2 genes to serious and violent delinquency among adolescents and young adults. Hum. Genet. 2007; 121(1):125-136.

Caspi, A, Sugden K, Moffitt TE, et al. Influence of life stress on depression; moderation by a polymorphism in the 5-HTT gene. Science. 2003;301(5631): 386-389.

Araya R, Hu X, Heron J, Enoch M-A, Evans J, Lewis G, Nutt D, Goldman D: Effects of stressful life events, maternal depression and 5-HTTLPR genotype on emotional symptoms in pre-adolescent children. Am J Med Genet. 2009; 150B:670-682.

Aslund C, Leppert J, Comasco E, Nordquist N, Oreland L, Nilsson K: Impact of the interaction between the 5HTTLPR polymorphism and maltreatment on adolescent depression: A population-based study. Behav Genet. 2009; 39:524-531.

Benjet C, Thompson RJ, Gotlib IH: 5-HTTLPR moderates the effect of relational peer victimization on depressive symptoms in adolescent girls. J Child Psychol Psychiatry. 2009; E-Pub.

Bukh JD, Bock C, Vinberg M, Werge T, Gether U, Vedel Kessing L: Interaction between genetic polymorphisms and stressful life events in first episode depression. J Affect Disord. 2009; E-Pub.

Carola V et al.: Identifying Molecular Substrates in a Mouse Model of the Serotonin Transporter x Environment Risk Factor for Anxiety and Depression. Biol Psychiatry 2008; 63:840-846.

Chen M, Joormann J, Hallmayer J, Gotlib: Serotonin transporter polymorphism predicts waking cortisol in young girls. Psychoneuroendocrinology 2009; 34:681-686.

Fox E, Ridgewell A, Ashwin C: Looking on the bright side: biased attention and the human serotonin transporter gene. Proc. R. Soc. B 2009; 276:1747-1751.

Eley TC, Sugden K, Corsico A, Gregory AM, Sham P, McGuffin P, Plomin R, Craig IW: Gene-environment interaction analysis of serotonin system markers with adolescent depression. Mol Psychiatry. 2004; 9:908.

Gillespie NA, Whitfield JB, Williams B, Heath AC, Martin NG: The relationship between stressful life events, the serotonin transporter (5-HTTLPR) genotype and major depression. Psychol Med. 2005; 35:101-111.

Goldman N: The serotonin transporter polymorphism (5-HTTLPR): Allelic variation and links with depressive symptoms. Depress Anxiety. In Press.

Gotlib I et al.: HPA Axis Reactivity: A Mechanism Underlying the Associations Among 5-HTTLPR, Stress, and Depression. Biol Psychiatry 2008; 63:847-851.

Kaufman J, Yang BZ, Douglas-Palumberi H, Houshyar S, Lipschitz D, Krystal JH, Gelernter J: Social supports and serotonin transporter gene moderate depression in maltreated children. Proc Natl Acad Sci U S A. 2004; 101:17316-17321.

Kendler KS, Kuhn JW, Vittum J, Prescott CA, Riley B: The interaction of stressful life events and a serotonin transporter polymorphism in the prediction of episodes of major depression: A replication. Arch Gen Psychiatry. 2005; 62:529-535.

Kumsta R, Stevens S, Brookes K, Schlotz W, Castle J, Beckett C, Kreppner J, Rutter M, Sonuga-Barke E: 5HTT genotype moderates the influence of early institutional deprivation on emotional problems in adolescence: Evidence from the English and Romanian Adoptee (ERA) study. In Review.

Laucht M, Treutlein J, Blomeyer D, Buchmann AF, Schmid B, Becker K, Zimmermann US, Schmidt MH, Esser G, Rietschel M, Banaschewski T: Interaction between the 5-HTTLPR serotonin transporter polymorphism and environmental adversity for mood and anxiety psychopathology: Evidence from a high-risk community sample of young adults. Int J Neuropsychopharmacol. 2009; 12:737-747.

Lenze E. et al.: Association of the Serotonin Transporter Gene-Linked Polymorphic Region (5-HTTLPR) Genotype with Depression in Elderly Persons After Hip Fracture: AM J Geriatr Psychiatry 2005; 13:428-432.

Lotrich F et al.: Risk for Depression During Interferon-Alpha Treatment is Affected by the Serotonin Transporter Polymorphism. Biol Psychiatry 2009; 65:344-348.

Mandelli L et al.: Interaction Between Serotonin Transporter Gene, Catechol-O-Methyltransferase Gene and Stressful Life Events in Mood Disorders. Int J Neuropsychopharmacol 2007; 10:437-447.

McCaffery JM, Duan QL, Frasure-Smith N, Barhdadi A, Lesperance F, Theroux P, Rouleau GA, Dubé MP: Genetic predictors of depressive symptoms in cardiac patients. Am J Med Genet. 2009; 150B:381-388.

Mossner R, Henneberg A, Schmitt A, Syagailo YV, Grassle M, Hennig T, Simantov R, Gerlach M, Riederer P, Lesch KP: Allelic variation of serotonin transporter expression is associated with depression in Parkinson's disease. Mol Psychiatry. 2001; 6:350-352.

Ramasubbu R, Tobias R, Buchan AM, Bech-Hansen NT: Serotonin transporter gene promoter region polymorphism associated with poststroke major depression. J Neuropsychiatry Clin Neurosci. 2006; 18:96-99.

Sudgen K, Arseneault L, Harrington H, Moffitt TE, Williams B, Caspi A: The serotonin transporter gene moderates the development of emotional problems among children following bullying victimization. In Review.

Uher R and McGuffin P: The Moderation by the Serotonin Transporter Gene of Environmental adversity in the Etiology of Depression: 2009 updated. Molecular Psychiatry 2010; 15: 18-22.

\* cited by examiner

SEQUENCE LISTING

```
<160> NUMBER OF SEQ ID NOS: 4

<210> SEQ ID NO 1
<211> LENGTH: 20
<212> TYPE: DNA
<213> ORGANISM: Homo sapiens

<400> SEQUENCE: 1
acagcctgac cgtggagaag                                                      20

<210> SEQ ID NO 2
<211> LENGTH: 20
<212> TYPE: DNA
<213> ORGANISM: Homo sapiens

<400> SEQUENCE: 2
gaacggacgc tccattcgga                                                      20

<210> SEQ ID NO 3
<211> LENGTH: 24
<212> TYPE: DNA
<213> ORGANISM: Homo sapiens

<400> SEQUENCE: 3
atgccagcac ctaaccccta atgt                                                 24

<210> SEQ ID NO 4
<211> LENGTH: 20
<212> TYPE: DNA
<213> ORGANISM: Homo sapiens

<400> SEQUENCE: 4
ggaccgcaag gtgggcggga                                                      20
```

METHOD FOR ASSESSING PREDISPOSITION TO DEPRESSION

CROSS-REFERENCE TO RELATED APPLICATIONS

This application claims the benefit of U.S. Provisional Application No. 60/486,640 filed Jul. 11, 2003. This application is incorporated herein by reference in its entirety.

STATEMENT REGARDING FEDERALLY SPONSORED RESEARCH OR DEVELOPMENT

The present invention was made with US Government funding provided by National Institutes of Health, National Institute of Mental Health, Grant Nos. MH 49414 and MH 45070. The United States Government has certain rights in the invention.

BACKGROUND OF THE INVENTION

A decades long search for conclusive evidence of interplay between genotype and environment to yield a behavioral effect has not succeeded. It has long been postulated that such interplay will exist, but these have not been demonstrated prior to the invention described herein. See Rutter, M. and J. Silberg, "Gene-Environment Interplay in Relation to Emotional and Behavioral Disturbance," *Ann. Rev. Psychol.* 53:463-490 (2002). Demonstration of such an effect would be of great interest to psychiatrists, psychologists, social workers, law enforcement and justice administration personnel, and others involved with behavioral issues.

The invention described in this application relates, in part, to an interaction between a pathogenic environmental risk factor (childhood maltreatment) and a genotype (allelic profile at a genetic locus that encodes monoamine oxidase A [MAOA]). Childhood maltreatment is a universal risk factor for antisocial behavior. Boys who experience abuse—and more generally, those exposed to erratic, coercive, and punitive parenting—are at risk of developing conduct disorder, evidencing antisocial personality symptoms, and of becoming violent offenders. The earlier children experience maltreatment, the more likely they are to develop these problems. But there are large differences among children in their response to maltreatment. Although maltreatment increases the risk of later criminality by about 50%, most maltreated children do not become delinquents or adult criminals. The reason for this variability in response is largely unknown, but it may be that vulnerability to adversities is conditional upon genetic susceptibility factors.

The MAOA gene, located on the X chromosome (Xp11.23-11.4), encodes the MAOA enzyme, which metabolizes, and renders inactive, neurotransmitters such as norepinephrine (NE), serotonin (5-HT) and dopamine (DA). Genetic deficiencies in MAOA activity have been linked with aggression in mouse and man. Increased aggression, and increased levels of brain NE, 5-HT, and DA, were observed in a transgenic mouse line in which the gene encoding MAOA was deleted, and aggression was normalized by restoring MAOA expression. In humans, a null allele at the MAOA locus was linked with male antisocial behavior in a Dutch kindred. Because MAOA is an X-linked gene, affected males with a single copy produced no MAOA enzyme—effectively, a human knockout. However, this mutation is extremely rare. Evidence for an association between MAOA and aggressive behavior in the human general population remains inconclusive.

Animal studies document that maltreatment stress (e.g., maternal deprivation, peer rearing) in early life alters NE, 5-HT, and DA neurotransmitter systems in ways that can persist into adulthood and influence aggressive behaviors. In humans, altered NE and 5-HT activity are linked to aggressive behavior. Maltreatment has lasting neurochemical correlates in human children. Deficient MAOA activity may dispose the organism toward neural hyper-reactivity to threat, as evidenced by the inhibitory action of phenelzine injections which inhibit the action of monoamine oxidase and prevented rats from habituating to chronic stress. Low MAOA activity may be particularly problematic early in life, because there is insufficient MAOB (a homolog of MAOA with broad specificity to neurotransmitter amines) to compensate for an MAOA deficiency.

In a related aspect, the invention relates in part to an interaction between a second pathogenic environmental risk factor (life stress) and a second genotype (allelic profile at a genetic locus that encodes 5-HTT), where the second genotype is conditionally associated with depression and the second environmental risk factor conditionally moderates the association.

Depression is among the top five leading causes of disability and disease burden throughout the world. Across the life span, stressful life events that involve threat, loss, humiliation, or defeat influence the onset and course of depression. But not all people who encounter a stressful life experience succumb to its depressogenic effect. Diathesis-stress theories of depression predict that individuals' sensitivity to stressful events depends on their genetic makeup. Behavioral genetics research supports this prediction, documenting that the risk of depression following a stressful event is elevated among people who are at high genetic risk and diminished among those at low genetic risk. But whether specific genes exacerbate or buffer the effect of stressful life events on depression is unknown.

The serotonin system is the target of selective serotonin re-uptake inhibitor drugs that are effective in treating depression. The serotonin transporter has received particular attention because it is involved in the re-uptake of serotonin at brain synapses. The promoter activity of the 5-HTT gene, located on 17q11.2, is modified by polymorphic sequence elements within the proximal 5' regulatory region, designated the 5-HTT gene-linked polymorphic region (5-HTTLPR). A short ('s') allele in the 5-HTTLPR is associated with lower transcriptional efficiency of the promoter than is a long ('l') allele.

Evidence for an association between the short promoter variant and depression is inconclusive. Although the 5-HTT gene may not be directly associated with depression, it could moderate the serotonergic response to stress, for several reasons. First, in mice with disrupted 5-HTT, homozygous and heterozygous (5HTT −/−, +/−) strains exhibit more fearful behavior and greater increases in the stress hormone adrenocorticotropin (plasma ACTH) in response to stress compared to homozygous (5HTT +/+) controls, but in the absence of stress no differences related to genotype are observed. Second, in rhesus macaques, whose length variation of the 5-HTTLPR is analogous to that of humans, the short allele is associated with decreased serotonergic function (lower CSF 5-HIAA concentrations) among monkeys reared in stressful conditions, but not among normally reared monkeys. Third, human neuroimaging research suggests that the stress response is mediated by variations in the 5-HTTLPR. Humans with one or two copies of the short allele exhibit greater amygdala neuronal activity to fearful stimuli compared to individuals homozygous for the long allele.

BRIEF SUMMARY OF THE INVENTION

The present invention relates, in part, to diagnostic methods for assessing whether a human or a non-human subject is predisposed to a mental disorder phenotype associated with an allele of a brain-functional gene, where a pathogenic environmental risk factor moderates the association between the allele and the phenotype. It is important in the methods to ascertain whether a subject assessed for predisposition to the disorder phenotype has either or both of the contributing genetic and environmental risk factors, or is vulnerable to the environmental risk factor. Similarly, it is important to ascertain the likelihood that a disorder phenotype seen in a subject arises as a result of genetic or environmental influences or both.

Results obtained from such a diagnostic method are advantageously employed in developing appropriate interventions for the subject, prior to or subsequent to the subject experiencing the pathogenic environmental risk factor, or both. In either case, the appropriate pre-emptive or therapeutic intervention can be adjusted in keeping with the findings of the diagnostic methods. At least two related scenarios are envisioned. Pre-emptive interventions designed to prevent or minimize exposure to the environmental pathogen can include counseling a subject to avoid the pathogen, or, if that is not possible, providing the subject with a pre-emptive treatment strategy when the pathogen is apparent. Therapeutic interventions after exposure to the pathogen can include pharmacological therapy and counseling therapy. One can also select one or more populations of individuals for participation in a pharmaceutical screening protocol on the basis of a combination of the genotype and experience with the pathogenic environmental risk factor by the individuals.

In another aspect, the present invention is summarized in that in a first diagnostic method for assessing predisposition of a subject to a disorder phenotype having an association with an at-risk allele of a brain-functional gene, the association being conditioned by a pathogenic environmental risk factor status condition, where the subject that has experienced, or is at risk of experiencing, the environmental risk factor, the method includes the steps of determining whether the subject carries one or more copies of an at-risk allele, and concluding that the subject is predisposed to the phenotype if the subject carries the at-risk allele.

In a related aspect, the present invention is summarized in that in a second diagnostic method for assessing predisposition of a subject to a disorder phenotype having an association with an at-risk allele of a brain-functional gene, the association being conditioned by a pathogenic environmental risk factor status condition, where the subject carries the at-risk allele, the method includes the steps of determining whether the subject has experienced or is at risk of experiencing the environmental risk factor, and concluding that the subject is predisposed to the phenotype if the subject has experienced or is at risk of experiencing the environmental risk factor.

In yet another related aspect, the present invention is summarized in that in a third diagnostic method for assessing predisposition of a subject to a disorder phenotype having an association with an at-risk allele of a brain-functional gene, the association being conditioned by a pathogenic environmental risk factor status condition, the method includes the steps of determining whether the subject carries the at-risk allele and determining whether the subject has experienced or is at risk of experiencing the environmental risk factor, the subject being predisposed to the phenotype if the subject carries the at-risk allele and has experienced or is at risk of experiencing the environmental risk factor.

The invention also relates to methods for discovering, in the first instance, a conditional association between an allele of a brain-functional gene and a mental disorder phenotype, where the association is conditioned upon a pathogenic environmental risk factor status, such a conditional association being suitable for evaluation in the diagnostic and preventative methods of the invention. One can employ the identified at-risk allele of a brain-functional gene and pathogenic environmental risk factor in any of the disclosed diagnostic methods for assessing whether an individual is predisposed to the associated disorder phenotype.

In a related aspect, such a discovery method includes the steps of identifying at least one a mental disorder phenotype having high or very high heritability coefficient, identifying a pathogenic environmental risk factor that operates on the at least one phenotype via non-genetic means and having at least higher and lower risk status conditions; ascertaining in a population of individuals an allelic profile for at least one brain-functional gene having an at-risk allele and at least one other allele, and selecting from the at least one disorder phenotype a disorder phenotype that correlates with statistical significance in the population with the at-risk allele only under the higher risk status condition, but which lacks statistically significant correlation with the at-risk allele under the lower risk status condition.

Methods for identifying a conditional association between an allele and a disorder phenotype, where the association is conditioned by a pathogenic environmental risk factor status condition, employ the well-characterized method of moderated multiple regression analysis to test for statistical interaction effects. See, Aiken, L. S. and S. G. West, *Multiple regression: Testing and Interpreting Interactions*, Thousand Oaks, Calif.: Sage (1991) and Long, S. J., *Regression Models for Categorical and Limited Dependent Variables*, Thousand Oaks, Calif.: Sage (1997), both incorporated by reference as if set forth herein in its entirety. Accordingly, it will be apparent that the present invention disclosure puts into the hands of the skilled artisan the ability to construct a matrix in which any or all of a plurality of pathogenic environmental risk factors, disorder phenotypes, and known alleles of brain-functional genes can be evaluated as described herein, preferably using a computing device for routine computations, to identify other conditional interactions between alleles and disorder phenotypes, where the interactions are conditioned by a pathogenic environmental risk factor status condition. Although such an analysis is necessarily complex, no undue experimentation is required, as all necessary information is either readily available to the skilled artisan or can be acquired by careful data acquisition and analysis as the inventors here describe.

In an important aspect of the invention, a mental disorder phenotype suitable for evaluation in a diagnostic method of the invention is a behavioral disorder phenotype (e.g., antisocial behavior or psychosis), an emotional disorder phenotype (e.g., depression or anxiety), or a cognitive disorder phenotype (e.g., dementia or reading disability), as those terms are defined in the Diagnostic and Statistical Manual of Mental Disorders ("DSM"), in which genetic variation in a population accounts for a high or very high proportion of total phenotypic population variation. This "heritability coefficient" (h-squared), a known measure of the likelihood that interactions between at least one gene and at least one environmental risk factor are affecting the phenotype, can be calculated by evaluating how much more similar the behavioral phenotype is for monozygotic (MZ) twin pairs than for dizygotic (DZ) twin pairs, using, e.g., newly collected data or data from prior published studies. A disorder phenotype is suited for further consideration in the methods of the invention when the heritability coefficient is greater than about 30% (high), and is preferably greater than 50% (very high). At a heritability coefficient of, e.g., 30%, 30% of variation in the human population can be explained by genes and their interactions with environmental pathogens, while the other 50% is explained by direct environmental effects that are not conditional on genes. The fourth edition of the DSM (DSM-IV), the current version as of the application date, is incorporated by reference as if set forth herein in its entirety. It will be appreciated, however, that DSM is updated periodically and that the principles of the invention will apply with equal force to mental disorder phenotypes described and cataloged in subsequent editions, as well.

An exemplary mental disorder phenotype of interest in the methods of the invention is antisocial behavior disorder, vis juvenile conduct disorder (CD, manifested by children) and antisocial personality disorder (ASPD, manifested by adults), as specified in the DSM. Measures of antisocial outcomes can include: (1) psychiatric diagnosis of juvenile conduct disorder as specified in the DSM (persistent fighting, bullying, lying, stealing, cruelty to people or animals, vandalism, and disobeying rules), (2) official court records of conviction for violent offenses (assault, robbery, rape, domestic violence, homicide), (3) aggressive personality traits (willingness to harm others for own advantage, interest in and enjoyment of violent material), and (4) symptoms of adult antisocial personality disorder as specified in the DSM (a long-term history of repeated law violations, deceitfulness, conning, impulsivity, physical aggression, and irresponsibility with respect to jobs, spouse, or children, plus lack of remorse).

In a related important aspect of the invention, a pathogenic environmental risk factor is a non-genetic risk factor that is shown to increase risk of psychiatric disorder, and which is conditional on genotype. For example, in an exemplified embodiment, the environmental risk factor is a psychological trauma or psychosocial stress that operates on the disorder phenotype via non-genetic means. In accord with this embodiment, the pathogenic environmental risk factor is considered to be present in a subject if the subject has experienced the psychological trauma or psychosocial stress to an extent considered to be clinically significant in accord with the guidelines set forth in the DSM (e.g., in DSM-IV at pages 29-30 "Axis IV: Psychosocial and environmental problems"). In other embodiments, the environmental risk factor need not be psychological, but can include, without limitation, such varied risk factors as a subject's unhealthy diet, exposure to an infectious or toxic agent, experience with a pharmacological agent (including a natural or a synthetic drug), medical trauma or injury, and the like.

It is duly noted that a pathogenic environmental risk factor can be a predictive risk factor for a plurality of disorders, some having a genetic component and others having no such component. Nevertheless, an important aspect of a pathogenic environmental risk factor suitable for consideration in the methods of the invention is that the risk factor be predictive of the disorder phenotype of interest for, at least in part, non-genetic reasons. Although one can identify candidate risk factors by combing the existing literature for environmental risk factors purported to statistically predict a disorder phenotype, the methods of the invention presuppose an exclusion of those risk factors in which an apparent environmental risk factor masks a genetic risk factor operating on the disorder phenotype. It is noted that a pathogenic environmental risk factor is allowed to predict psychiatric outcome for genetic reasons in part if it also has proven environmental reasons. Some risk factors will involve both genetic and environmental reasons. However, a risk factor cannot be environmental if it predicts an outcome for only genetic reasons.

Moreover, one need not rely upon previously identified pathogenic environmental risk factors for use in the methods of the invention, but can instead identify novel pathogenic environmental risk factors, as long as risk factors having a hidden genetic risk component that operates on the disorder phenotype are excluded from use in the method by employing suitable research designs. Various research designs are described in Rutter, M. et al., "Testing Hypotheses on Specific Environmental Causal Effects on Behavior," *Psychological Bulletin* 127:291-324 (2001), incorporated by reference as if set forth herein in its entirety.

In still another important and a related aspect, a suitable allele of a gene that interacts with a pathogenic environmental risk factor operating upon a disorder phenotype having a high or very high heritability coefficient is an allele of a gene having brain functionality, as the term is understood in the art. Several non-limiting examples of genes having brain functionality are genes expressed in a cell type known to act in the brain, genes associated with variation in size of a brain structure, genes associated with concentration of a neurotransmitter in the brain, genes associated with brain responses to stimuli as assessed by an imaging method such as magnetic resonance imaging, and genes which when altered affect behavior of a human or non-human animal, such as a mammal or a rodent. The skilled artisan will appreciate that brain-functionality can be documented by various research methods such as biochemical analysis of brain tissue or cells obtained from human and non-human animals, as well as research on living non-human animals.

A plurality of alleles having distinct brain-functionality (e.g., high and low levels of expression in the brain, or, e.g., high, moderate and low levels of expression in the brain) can arise from one or more polymorphisms in a region of a gene that encodes a polypeptide or can be in a regulatory control sequence that affects expression of the polypeptide, such as a promoter or polyadenylation sequence. Alternatively, relevant alleles can arise from one or more polymorphism at a locus distal to a gene having a direct effect in the identified behavior, wherein the product of that distal locus has an indirect effect on the behavior. A relevant allele can affect a polypeptide at a transcriptional or a translational level and can affect a polypeptide's transcription rate, translation rate, degradation rate, or activity. Differences between alleles at a brain-functional gene can be characterized in a sample from a subject or from a plurality of subjects by methods for assaying any of the foregoing that are well-known to the skilled artisan. Such methods can include, but are not limited to measuring an amount of an encoded polypeptide and measuring the potential for a polynucleotide sequence to be expressed. Assay methods can detect proteins or nucleic acids directly or indirectly. One can evaluate the suitability of an upstream promoter region for directing transcription of a coding region of the polynucleotide that encodes a polypeptide or can evaluate the suitability of the coding region for encoding a functional polypeptide. The assay methods are specifically contemplated to include screening for the presence of particular sequences or structures of nucleic acids or polypeptides using, e.g., any of various known microarray technologies.

It will be fully appreciated by the skilled artisan that the allele need not have previously been shown to have had any link or association with the disorder phenotype. Instead, an allele and a pathogenic environmental risk factor can interact to predict a predisposition to a disorder phenotype even when neither the allele nor the risk factor bears any direct relation to the disorder phenotype. This aspect of the invention is depicted in the accompanying detailed description of a preferred embodiment, where hidden effects of alleles were revealed only when the environmental risk factor variable was included in the analysis.

A brain-functional gene of interest is the gene for the neurotransmitter-metabolizing enzyme monoamine oxidase A (MAOA). The gene is known to have two alleles, characterized by a low level and a high level of MAOA protein in the brain, respectively. Genetic deficiencies in MAOA activity have been linked with aggression in mice and in humans, as was noted in the Background of the Invention. However, no conclusive association exists between a "low activity" MAOA allele and such behavior in the human population generally. Moreover, this genotype does not by itself predict violent or antisocial behavior. About ⅓ of human males carry a low-activity MAOA allele.

In another related aspect, the invention is summarized in that a particular embodiment of a diagnostic method of the invention is recognized when the higher risk pathogenic environmental risk factor status is experience of a childhood psychological trauma, the at-risk allele is a "low activity" allele of the human monoamine oxidase A gene that reduces expression of the monoamine oxidase A protein relative to normal level, and the conditional disorder phenotype is antisocial behavior disorder. A subject is predisposed to the disorder when the subject carries the "low activity" allele and has experienced or is at risk of experiencing the trauma. A "low activity" allele of MAOA gene is well known and has been characterized. See Detailed Description for characterization.

It will also be appreciated that the invention facilitates identifying in an individual a positive or negative trait or strength that could warrant counseling the subject to pursue or avoid a particular type of employment. For example, an individual having no identified predisposition toward antisocial behavior might be encouraged toward a career in law enforcement.

Similarly, the link appreciated by the inventors facilitates testing of individuals who have yet to experience (or may never experience) the relevant environmental risk factor, such that an individual determined to carry the subject genetic attribute can be counseled or directed to avoid the environmental risk factor. Additionally, the subject can receive therapy of a psychological or pharmaceutical nature. Prior to the invention by the applicants, the skilled person would not have appreciated the need for vigilant monitoring of such individuals in that regard.

In still another embodiment, a brain functional gene of interest is the 5-HTT serotonin transporter gene, located on human chromosomal locus 17q11.2, which is responsible for preventing too much neurotransmitter in the space between nerve cells. The gene is known to have two polymorphic alleles (SLC6A4) in the promoter region of the gene (5'HTTLPR) that modifies expression of the gene. The short ('s') allele in the 5-HTTLPR is associated with lower transcriptional efficiency of the promoter than is the long ('l') allele (11).

Evidence for an association between the short promoter allele and depression is inconclusive. Although the 5-HTT gene may not be directly associated with depression, it could moderate the serotonergic response to stress. Three lines of experimental research suggest this hypothesis of a Gene× Environment (G×E) interaction. First, in mice with disrupted 5-HTT, homozygous and heterozygous (5HTT −/−, +/−) strains exhibit more fearful behavior and greater increases in the stress hormone adrenocorticotropin (plasma ACTH) in response to stress compared to homozygous (5HTT +/+) controls, but in the absence of stress no differences related to genotype are observed (13). Second, in rhesus macaques, whose length variation of the 5-HTTLPR is analogous to that of humans, the short allele is associated with decreased serotonergic function (lower CSF 5-HIAA concentrations) among monkeys reared in stressful conditions, but not among normally reared monkeys (14). Third, human neuroimaging research suggests that the stress response is mediated by variations in the 5-HTTLPR. Humans with one or two copies of the short allele exhibit greater amygdala neuronal activity to fearful stimuli compared to individuals homozygous for the long allele (15). Taken together, these findings suggest the hypothesis that variations in the 5-HTT gene moderate psychopathological reactions to stressful experiences.

In another related aspect, the invention is summarized in that a particular embodiment of a diagnostic method of the invention is recognized when the higher risk pathogenic environmental risk factor status is experience of stressful life events, the at-risk allele is a short allele of the 5-HTT gene. In contrast, the long allele confers protection against stressful life events, such that the capacity of stressful life events to cause an episode of clinical depression is conditional on which of the two versions of the gene are carried. A subject is predisposed to clinical depression when the subject carries the short 5-HTT allele and has experienced or is at risk of experiencing stressful life events. The short allele of 5-HTT gene is well known and has been characterized. See Detailed Description for characterization.

It will be appreciated that in another aspect the invention relates to therapeutic intervention for a subject determined by a method of the invention to be predisposed to depression. Such interventions can include counseling and pharmaceutical therapies, in particular, administration of at least one anti-depressive agent to the subject when at risk for experiencing a stressful life event, at the time of a stressful life event or after a stressful life event has occurred.

In yet another related embodiment, the invention is summarized in that a kit for use with a preventative or diagnostic method of the invention comprises (1) a questionnaire that solicits input about a subject relevant to the subject's experience with at least one of (a) a pathogenic environmental risk factor and (b) a disorder phenotype, and (2) a system for obtaining from the subject a sample suitable for producing an allelic profile of at least one brain-functional gene. Optionally, a kit of the present invention can further comprise an assay system for producing the allelic profile of at least one brain-functional gene.

In a preferred embodiment, allelic profiling can be accomplished using a nucleic acid microarray, which can also be commercialized alone or in combination with one or more of the aforementioned kit components. The genetic diagnostic testing field is rapidly evolving and, as such, the skilled artisan will appreciate that a wide range of profiling tests exist, and will be developed, to determine the allelic profile of individuals in accord with the invention.

It is an object of the present invention to provide a systematic method for finding a significant predisposition to a behavior characterized by the combination of an identified allele at a genetic locus and an identified environmental stimulus.

It is an advantage of the present invention that the discovery methods of the invention yield quantitative indications of statistical significance in the Gene×Environment interaction term that instructively guide the artisan in development of diagnostic methods of the invention.

It is a feature and an advantage of the invention that an allele and a pathogenic environmental risk factor can interact to predict a predisposition to a disorder even when neither the allele nor the risk factor bears any direct relation to the disorder. Accordingly, even if the prior knowledge in the art does not show a relationship between an allele of a brain-functional gene and a disorder phenotype, one can still use the discovery methods of the invention to ascertain a previously hidden link between the allele and the disorder.

It is a related feature of the invention that the discovery methods determine whether a disorder phenotype correlates with the allele in a high risk environmental condition while not correlating with the allele in a low risk environmental condition. Accordingly, the effect of the allele is conditional upon the environment. In other words, the allele moderates the effect of the environment on the behavior disorder phenotype.

Other objects, advantages and features of the present invention will become apparent upon consideration of the following detailed description.

DETAILED DESCRIPTION OF THE INVENTION

Example 1

Figure 1:
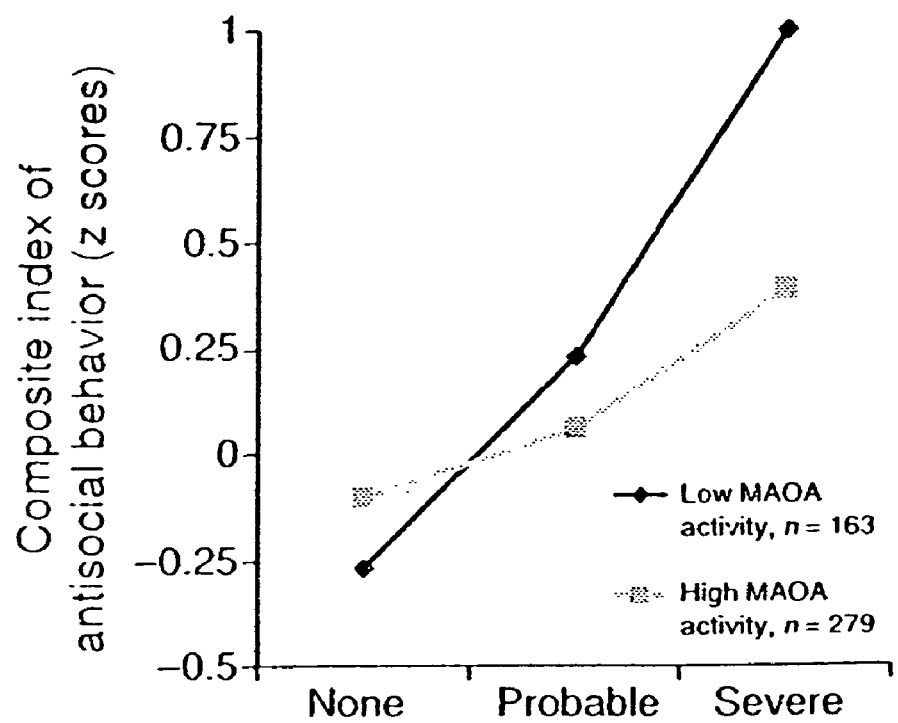
FIG. 1 depicts the means on the composite index of antisocial behavior as a function of MAOA activity and a childhood history of maltreatment. MAOA activity is the gene expression level associated with allelic variants of the functional promoter polymorphism, grouped into low and high activity; childhood maltreatment is grouped into 3 categories of increasing severity. The antisocial behavior composite is standardized (z-score) to a M=0 and SD=1; group differences are interpretable in SD unit differences.

We studied a large sample of male children from birth to adulthood to determine why some children who are maltreated grow up to develop antisocial behavior whereas others do not. A functional polymorphism in the gene encoding the neurotransmitter metabolizing enzyme monoamine oxidase A (MAOA) was found to moderate the effect of maltreatment. Maltreated children with a genotype conferring high levels of MAOA expression were less likely to develop antisocial problems. These findings may partly explain why not all victims of maltreatment grow up to victimize others, and they provide epidemiological evidence that genotypes can moderate children's sensitivity to environmental insults. In this study, individual differences at a functional polymorphism in the promoter of the monoamine oxidase A (MAOA) gene were used to characterize genetic susceptibility to maltreatment and to test whether the MAOA gene modifies the influence of maltreatment on children's development of antisocial behavior.

Based on the hypothesis that MAOA genotype can moderate the influence of childhood maltreatment on neural systems implicated in antisocial behavior, we tested whether antisocial behavior would be predicted by an interaction between a gene (MAOA) and an environment (maltreatment). A well-characterized variable number tandem repeat (VNTR) polymorphism exists at the promoter of the MAOA gene, which is known to affect expression. We genotyped this polymorphism in members of the Dunedin Multidisciplinary Health and Development Study, a sample without population stratification confounds. The history of the Study is described in P. A. Silva, W. Stanton, Eds. *From Child to Adult: The Dunedin Study* (Oxford University Press, 1996). This birth cohort of 1,037 children (52% male) has been assessed at ages 3, 5, 7, 9, 11, 13, 15, 18, 21, and was virtually intact (96%, N=499 males) at age 26 years.

Research Sample. The Dunedin longitudinal study was constituted at age 3 when the investigators enrolled 91% of the consecutive births between April 1972 and March 1973 in Dunedin, New Zealand. Cohort families represent the full range of socioeconomic status in the general population of New Zealand's South Island. Follow-ups have been carried out at ages 3, 5, 7, 9, 11, 13, 15, 18, 21, and most recently at age 26, when we assessed 96% of the living cohort members (N=499 males). At each age, participants are brought back to the research unit within 60 days of their birthday for a full day of individual tests and interviews. These data are supplemented by questionnaires completed by persons who know the Study members well and by official record searches.

DNA extraction and genotyping. At age 26, DNA was obtained from 953 Study members (97% of those assessed at that age; 51% male); 93% of DNA samples were obtained via blood and 7% via buccal swabs for those not wishing to undergo phlebotomy. DNA was extracted from blood samples using standard procedures. A modified procedure was used to extract DNA from buccal cells. Primer sequences are described by Sabol et al., namely MAO APT1 (5'-ACAGCCTGACCGTGGAGAAG-3'; SEQ ID NO:1) and MAO APB1 (5'-GAACGGACGCTCCATTCGGA-3'; SEQ ID NO: 2), although here MAO APT1 was 5'-labelled with the TET fluorophore. PCR was carried out on a PTC-225 DNA engine (MJ Research), using the following cycling conditions: initial 2-min denaturing step at 95° C., followed by 35 cycles of 94° C. for 1 min, 58.2° C. for 1 min and 72° C. for 1 min 30 secs, and a final extension phase of 72° C. for 5 min. Reactions were performed in 25 µl GeneAmp PCR Buffer I (PE Applied Biosystems), 1.5 mM $MgCl_2$, 50 ng of genomic DNA, 10 pmols of each primer, 0.33 mM dNTPs and 1.5 units of Native Taq (Promega). PCR products were assayed on an Applied Biosystems 377 Genetic Analyzer (PE Applied Biosystems), set up in genotyping mode, using 4.25% w/v polyacrylamide gel (Amresco) and TAMRA-labelled GS500 (PE Applied Biosystems) size standard. Results were analyzed using GeneScan v2.1 and Genotyper v1.1 software (Applied Biosystems).

Table 1 shows the allele frequencies observed among non-Maori members of our Study. The genotypes were classified according to previous results showing that an optimum sequence length of 3.5 or 4 repeats results in high expression levels. In terms of expression, all studies agree on the functional classification of the two most common alleles, i.e. 3 repeats (low activity) and 4 repeats (high activity). These two alleles account for 95.7% of our sample. Of rare alleles, both Sabol et al. and Deckert et al. assayed the 3.5 repeat with the same result (high activity), whereas a discrepancy arises for the 5 repeat. We chose the classification of Sabol et al. as they assayed 3 cell lines as opposed to one. However, we carried out analyses using both classifications and observed the same effects. The rare 2 repeat, of which only 1 exists in our sample, was classified as low activity due to its short length.

TABLE 1

The Dunedin sample does not differ significantly from published frequencies of alleles (5, 7) at the MAO A promoter locus, $X^2$ (4) = 6.21, p = 0.184.

| Number of repeats at MAOA promoter polymorphism | 2 | 3 | 3.5 | 4 | 5 |
|---|---|---|---|---|---|
| Number (and percent) of alleles in Dunedin sample males, n (chromosomes) = 442 | 1 (0.2) | 149 (33.7) | 5 (1.1) | 274 (62.0) | 13 (2.9) |
| Number (and percent) of alleles in Caucasian controls, n (chromosomes) = 1940 | 3 (0.2) | 658 (33.9) | 9 (0.5) | 1238 (63.8) | 32 (1.6) |

Population stratification can probably be ruled out as a confounding factor in this study. First, cohort members reporting Maori ethnicity (7%) were not included in our analysis. Second, Caucasian study members reported the ethnicity of all four grandparents, and only 4% reported 1 or 2 non-European grandparents. Third, allele frequencies among Caucasian study members matched closely frequencies reported in Caucasian samples. As a final check for stratification we adopted a genomic control approach based on latent class analysis. One hundred individuals were selected at random from the sample and typed for 40 unlinked microsatellite markers. In a stratified sample one would expect to observe Hardy-Weinberg disequilibrium and linkage disequilibrium across the unlinked markers: our genomic control approach aimed to identify subpopulations (latent classes) such that within each there is Hardy-Weinberg and linkage equilibrium. In the current sample, however, there was no support for having more than one latent class, which is consistent with the sample being homogeneous.

Childhood maltreatment. Evidence of childhood maltreatment during the first decade of life (ages 3 to 11 years) was ascertained using behavioral observations, parental reports, and retrospective reports by Study members once they reached adulthood. First, mother-child interactions were observed during the child's age-3 assessment. The mother was rated by an observer on eight categories: mother's affect toward the child was consistently negative; harshness toward the child; rough, awkward handling of the child; no effort to help child; unaware or unresponsive to child's needs; indifferent to child's performance; demanding of child's attention; soiled, unkempt appearance of child). Mothers engaging in 2 or more such behaviors were classified as rejecting (16%), based on evidence that such maternal behavior is associated with increased risk of children's later antisocial behavior. Second, harsh discipline was measured at ages 7 and 9 using a checklist on which parents indicated if they engaged in ten disciplinary behaviors such as "smack him or hit him with something." Parents scoring in the top decile of the sample-wide distribution were classified as unusually harsh, relative to the culture in which this cohort grew up (10%), based on evidence that such parenting styles are associated with subsequent antisocial behavior of children. Third, changes in the person occupying the role of the child's primary caregiver were ascertained at each assessment. Children who experienced 2 or more such changes during the first decade of life were classified as having suffered disruptive caregiver changes (6%), based on evidence that such family changes are predictive of later antisocial behavior. Fourth, exposure to child physical abuse was assessed retrospectively at age 26 as part of an interview about victimization. Study members were classified as physically abused if they reported multiple episodes of severe physical punishment (e.g., strapping leaving welts; whipping with electric cords) resulting in lasting bruising or injury before age 11 (3%). Fifth, unwanted sexual contact was assessed retrospectively at age 26 as part of an interview about reproductive health. Study members were classified as sexually abused if they reported having their genitals touched, touching another's genitals, or attempted/completed sexual intercourse before age 11 (5%). The percentages of males experiencing physical and sexual abuse are consistent with rates reported elsewhere. We examined these maltreatment experiences based on evidence that they too are linked to antisocial behavior. We derived a cumulative exposure index for each child by counting the number of maltreatment experiences during the first decade of life; 64% of the children experienced no maltreatment, 28% experienced 1 indicator of maltreatment (hereafter referred to as "probable maltreatment"), and 8% experienced 2 or more indicators of maltreatment (hereafter "severe maltreatment").

Antisocial behavior outcomes in adolescence and in adulthood. We examined four different outcome measures of antisocial behavior, using information from independent data sources that were appropriate at different stages of development.

Conduct disorder was measured according to the criteria of the Diagnostic and Statistical Manual of Mental Disorders (DSM), which identify adolescents displaying a persistent pattern of behavior that violates the rights of others, including physical harm. A diagnosis of conduct disorder (using a 12-month reporting period for symptoms) was made in our longitudinal study when we assessed the research participants at each of four ages: ages 11, 13, 15, and 18. A 'lifetime' diagnosis was arrived at by establishing whether a Study member received the diagnosis at one or more of the four ages (according to the DSM, conduct disorder is not normally diagnosed after age 18).

Court records of violent convictions in adulthood were searched via the Australian and New Zealand Police for 97% of male Study members. Among Study males, 11% received 174 convictions for violent crimes (e.g., common assault, aggravated assault with intent to injure with weapon, domestic violence, manslaughter, rape).

A disposition toward violence was ascertained at age 26 as part of the Multidimensional Personality Questionnaire (MPQ) Aggression scale (e.g., "When I get angry I am ready to hit someone," "I admit that I sometimes enjoy hurting someone physically"). α reliability of the summed scale was 0.71.

Symptoms of antisocial personality disorder were ascertained at age 26, when informant reports about 95% of male Study members were collected by mailing a questionnaire to persons they nominated as "someone who knows you well". Informants were friends, partners, or family members. Informants described the Study members on seven cardinal symptoms: "has problems controlling anger," "blames others for own problems, "does not show guilt after doing something bad," "impulsive, rushes into things without thinking," "good citizen (reversed)," "does things against the law," and "gets into fights." Response options were "not a problem, "a bit of a problem,", and "yes, a problem." α reliability of the summed scale was 0.84.

Intercorrelations between the four outcomes ranged from 0.32 to 0.46. We fitted a common factor model to the four measures of antisocial behavior, using methods appropriate to the mixture of categorical and continuous measures. According to multiple fit indices, the model fit well ($\Pi^2$ (2)=2.56, p=0.28, CFI=0.99, RMSEA=0.02), with factor loadings ranging from 0.64 to 0.74, showing that all four measures index liability to antisocial behavior. On the basis of the factor analysis, we created a composite index of antisocial behavior by counting the number of antisocial outcomes observed for each Study member. This summary index counts whether they (a) met diagnostic criteria for adolescent conduct disorder, (b) were convicted for a violent crime, (c) scored in the top quartile of the distribution on a self-reported disposition toward violence, and (d) scored in the top quartile of the distribution on informant-reported antisocial personality disorder symptoms. We created this composite because the most reliable way to measure antisocial behavior is to aggregate multiple sources of information. We also report separate analyses of each of the four measures of antisocial behavior, in order to test whether the observed findings were robust or sensitive to the four different ways in which the antisocial phenotype was measured. A robust finding is one whose pattern should be observed irrespective of how antisocial behavior is measured.

The effects of MAOA activity, maltreatment, and their interaction on antisocial behavior were estimated in a moderated regression framework, using logistic regression for categorical outcomes (e.g., conduct disorder) and ordinary least squares (OLS) for continuous measures (e.g., personality disposition toward violence).

The full results are contained in Table 2. The interaction effect was consistent with the hypothesis that MAOA activity moderated the effect of maltreatment on antisocial outcomes. As shown in FIG. 1, the dose-response association between maltreatment and antisocial behavior was significantly weaker in the high-MAOA activity group than in the low-MAOA activity group. We probed the gene×environment interaction further and found that the difference in antisocial behavior between the high- and low-MAOA groups became larger at increasing levels of maltreatment. T-tests for these differences are as follows: t=−1.48, p=0.14 at no maltreatment, t=1.62, p=0.11 at probable maltreatment, and t=2.31, p=0.02 at severe maltreatment.

We further considered the possibility that the observed protective effect of high-MAOA activity could have been brought about because of individual differences in IQ. We considered this alternative hypothesis because complete and selective deficiency of enzymatic activity of MAOA was associated with mild mental retardation in the Dutch kindred, and low IQ is linked to high levels of antisocial behavior in the general population, including in this sample (r=−0.28, p<0.001). Therefore, the observed protective effect of high-MAOA activity could have been an epiphenomenon of higher IQ among males with this genotype. However, we found no IQ differences between males with low- and high-MAOA activity (M=107 (SD=14) vs. M=108 (SD=13), t(430)=−0.70, p=0.48), and no significant linear association between maltreatment and IQ in either the low-MAOA activity group, t(157)=−0.87, p=0.38, or the high-MAOA activity group, t(269)=0.93, p=0.34. We repeated the regression analysis shown in Supplementary Table 2 (first row), with the addition of IQ as a covariate. The interaction effect between MAOA and maltreatment remained statistically significant and of equivalent magnitude after controlling for IQ (b=−0.34, se=0.14, t=2.43, p=0.015).

social class differences between males with low- and high-MAOA activity, t(439)=0.90, p=0.37. We repeated the regression analysis shown in Supplementary Table 2 (first row), with the addition of social class as a covariate. The interaction effect between MAOA and maltreatment remained statistically significant and of equivalent magnitude after controlling for childhood social class origins (b=0.33, se=0.14, t=2.36, p=0.019).

The Study offers three advantages for testing gene-environment (G×E) interactions. First, in contrast to studies of adjudicated or clinical samples, the representative general population sample avoids potential distortions in association between variables. Second, the sample has well-characterized environmental adversity histories. Between ages 3-11 years, 8% of the Study children experienced "severe" maltreatment, 28% experienced "probable" maltreatment, and 64% experienced no maltreatment. (Maltreatment groups did not differ on MAOA activity, $\chi^2(2)$=0.38, p=0.82, suggesting that genotype did not influence exposure to maltreatment.) Third, the study has ascertained antisocial outcomes rigorously. Antisocial behavior is a complicated phenotype, and each method and data source used to measure it (e.g., clinical diagnoses, personality checklists, official conviction records) is characterized by different strengths and limitations. Using information from independent sources appropriate to different stages of development, we examined four outcome measures. Adolescent conduct disorder was assessed according to criteria of the Diagnostic and Statistical Manual of Mental Disorders (DSM); convictions for violent crimes were identified via the Australian and New Zealand police; a personal-

TABLE 2

Results of final regression analyses testing G × E interaction effects on antisocial outcomes. The Table presents final models with main effects and interactions entered simultaneously.

| | Predictor Variables | | | | | | | | | | | |
|---|---|---|---|---|---|---|---|---|---|---|---|---|
| Antisocial | MAOA | | | | Maltreatment[a] | | | | MAOA × Maltreatment | | | |
| Outcomes | B | se | t/z | p | b | se | t/z | P | b | se | t/z | p |
| Composite Antisocial Index | .16 | .11 | 1.45 | .15 | .54 | .11 | 4.73 | .001 | −.36 | .14 | 2.53 | .01 |
| Conduct Disorder (%) | .06 | .28 | .20 | .84 | .96 | .27 | 3.55 | .001 | −.63 | .33 | 1.87 | .06 |
| Violence Conviction (%) | .32 | .46 | .70 | .48 | 1.2 | .33 | 3.65 | .001 | −.83 | .42 | 1.95 | .05 |
| Disposition Toward Violence Scale | .11 | .11 | .95 | .35 | .35 | .12 | 3.04 | .003 | −.24 | .15 | 1.62 | .10 |
| Antisocial Personality Symptoms Scale | .22 | .12 | 1.90 | .06 | .45 | .12 | 3.74 | .001 | −.31 | .15 | 2.02 | .04 |

Childhood maltreatment was handled as a single quantitative variable in the regression analyses, ranging from no maltreatment to severe maltreatment.

Finally, we considered the possibility that the observed protective effect of high-MAOA activity could be brought about if children with this genotype were likely to be reared in favorable environments. As such, we introduced into our analyses a further environmental covariate, social class, that is associated with antisocial behavior, including in this sample (r=−0.46, p<0.001). The childhood social class variable used in our analyses is the average of the highest social class level of either parent, assessed repeatedly at the Study member's birth and ages 3, 5, 7, 9, 11, 13, and 15. This variable reflects the socioeconomic conditions experienced by the Study members while they grew up. There were no ity disposition toward violence was measured as part of a psychological assessment at age 26; symptoms of antisocial personality disorder were ascertained at age 26 by collecting information about the Study members from people they nominated as "someone who knows you well." A common-factor model fit the four measures of antisocial behavior well, with factor loadings ranging from 0.64 to 0.74, showing that all four measures index liability to antisocial behavior.

Using moderated regression analysis, we predicted scores on a composite antisocial index comprising the four measures of antisocial behavior (FIG. 1). The main effect of MAOA activity on the composite index of antisocial behavior was not significant (b=0.01, SE=0.09, t=0.13, p=0.89) while the main effect of maltreatment was significant (b=0.35, SE=0.07, t=4.82, p<0.001). The hypothesized interaction between MAOA activity and maltreatment revealed a significant G×E interaction (b=−0.36, SE=0.14, t=2.53, p=0.01). Probing the interaction within each genotype group showed that the effect of childhood maltreatment on antisocial behavior was significantly weaker among males with high-MAOA activity (b=0.24, SE=0.11, t=2.15, p=0.03) than among males with low-MAOA activity (b=0.68, SE=0.12, t=5.54, p<0.001).

Figure 2:
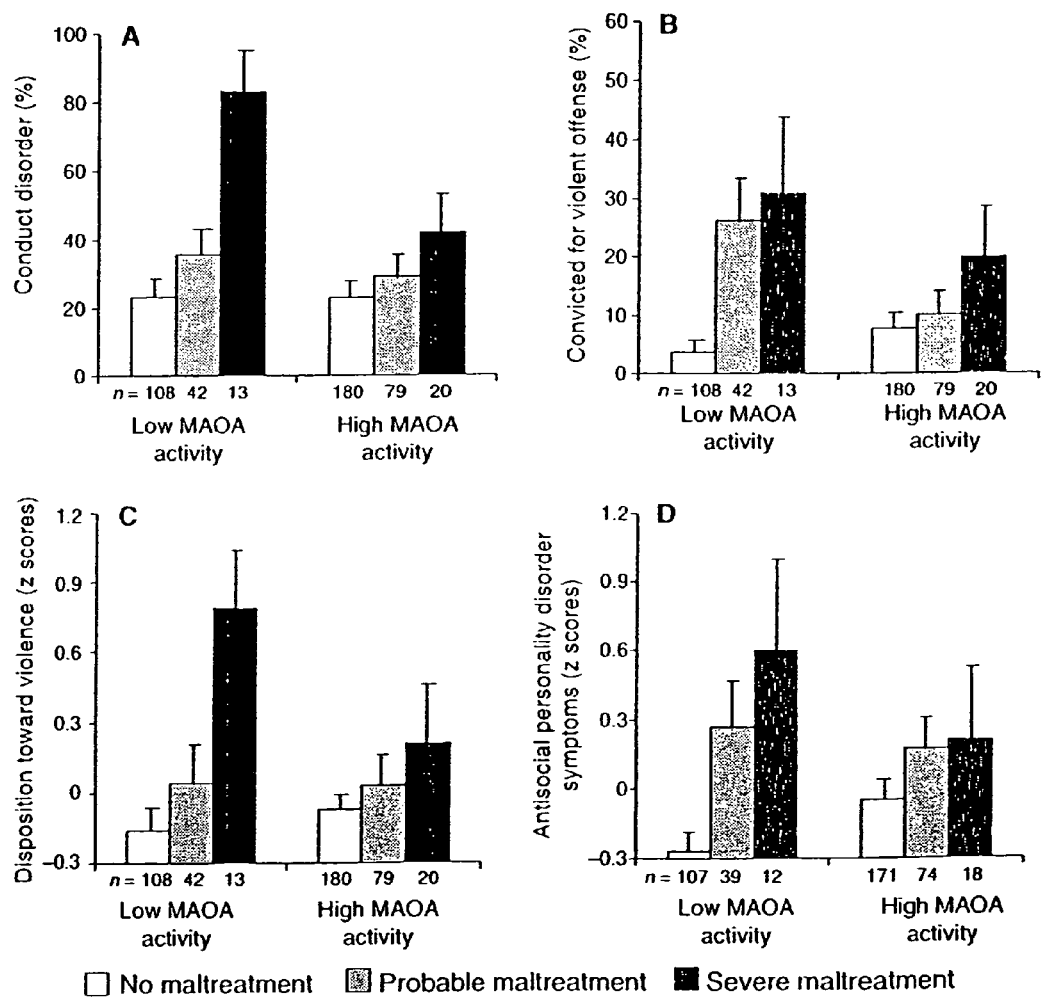
FIG. 2 depicts the association between childhood maltreatment and subsequent antisocial behavior as a function of MAOA activity. (A) Percentage of males (and standard errors) meeting diagnostic criteria for Conduct Disorder between ages 10-18. In a hierarchical logistic regression model, the interaction between maltreatment and MAOA activity was in the predicted direction, b=−0.63, SE=0.33, z=1.87, p=0.06. Probing the interaction within each genotype group showed that the effect of maltreatment was highly significant in the low-MAOA activity group (b=0.96, SE=0.27, z=3.55, p<0.001), and marginally significant in the high-MAOA group (b=0.34, SE=0.20, z=1.72, p=0.09). (B) Percentage of males convicted of a violent crime by age 26. The G×E interaction was in the predicted direction, b=−0.83, SE=0.42, z=1.955, p=0.05. Probing the interaction, the effect of maltreatment was significant in the low-MAOA activity group (b=1.20, SE=0.33, z=3.65, p<0.001), but was not significant in the high-MAOA group (b=0.37, SE=0.27, z=1.38, p=0.17). (C) Mean z-scores (M=0, SD=1) on the Disposition Toward Violence scale at age 26. In a hierarchical ordinary least squares (OLS) regression model, the G×E interaction was in the predicted direction (b=−0.24, SE=0.15, t=1.62, p=0.10); the effect of maltreatment was significant in the low-MAOA activity group (b=0.35, SE=0.11, t=3.09, p=0.002) but not in the high-MAOA group (b=0.12, SE=0.07, t=1.34, p=0.17). (D) Mean z-scores (M=0, SD=1) on the Antisocial Personality Disorder symptom scale at age 26. The G×E interaction was in the predicted direction (b=−0.31, SE=0.15, t=2.02, p=0.04); the effect of maltreatment was significant in the low-MAOA activity group (b=0.45, SE=0.12, t=3.83, p<0.001) but not in the high-MAOA group (b=0.14, SE=0.09, t=1.57, p=0.12).

We conducted further analyses to test if the G×E interaction was robust across each of the four measures of antisocial behavior that made up the composite index. For all four antisocial outcomes, the pattern of findings was consistent with the hypothesis that the association between maltreatment and antisocial behavior is conditional, depending on the child's MAOA genotype (G×E interaction p=0.06, 0.05, 0.10, and 0.04, respectively). For adolescent conduct disorder (FIG. 2A), maltreated males (including probable and severe cases) with the low-MAOA activity genotype were more likely than nonmaltreated males to develop conduct disorder by a significant odds ratio of 2.8 (95% CI:1.42-5.74). In contrast, among males with high-MAOA activity, maltreatment did not confer significant risk for conduct disorder (OR=1.54, 95% CI: 0.89-2.68). For adult violent conviction (FIG. 2B), maltreated males with the low-MAOA activity genotype were more likely than nonmaltreated males to be convicted of a violent crime by a significant odds ratio of 9.8 (95% CI:3.10-31.15). In contrast, among males with high-MAOA activity, maltreatment did not confer significant risk for violent conviction (OR=1.63, 95% CI=0.72-3.68). For self-reported disposition toward violence (FIG. 2C) and informant-reports of antisocial personality disorder symptoms (FIG. 2D), males with the low-MAOA activity genotype who were maltreated in childhood had significantly elevated antisocial scores relative to their low-MAOA counterparts who were not maltreated. In contrast, males with high-MAOA activity did not have elevated antisocial scores, even when they had experienced childhood maltreatment.

These findings provide initial evidence that a functional polymorphism in the MAOA gene moderates the impact of early childhood maltreatment on the development of antisocial behavior in males.

This study focused on males because their single X chromosome yields two straightforwardly characterized MAOA genotypes: high-activity (63% in this sample) and low-activity (37%). Females, having two copies of the X chromosome, fall into two homozygous groups, high-high (42% in this sample), low-low (12%), and a third heterozygous group, low-high (46%), that cannot be characterized with certainty because it is not possible to determine which of the two alleles is inactivated for each female participant. Given the rarity in females of both the low-low genotype (12%) and severe antisocial outcomes, such as violent conviction (2%), our cohort of 481 females, 11% of whom were severely maltreated, was too small to support all of the analyses reported here for males. However, adolescent conduct disorder could be analyzed, revealing that girls with the low-MAOA activity genotype were more likely to develop conduct disorder by a significant odds ratio of 5.5 (95% CI:1.0-32.0) if they were maltreated. In contrast, among girls with high-MAOA activity, maltreatment did not confer significant risk for conduct disorder (OR=1.7, 95% CI: 0.75-4.2). This suggests that high-MAOA activity exerts a protective influence against maltreatment for girls as well as boys, and raises the possibility that further research into X-linked genotypes may help to explain one of the least understood facts about serious antisocial behavior: the sex difference.

The findings have implications for research and clinical practice. With regard to research in psychiatric genetics, knowledge about environmental context might help gene-hunters refine their phenotypes. Genetic effects in the population may be diluted across all individuals in a given sample, if the effect is apparent only among individuals exposed to specific environmental risks. With regard to research on child health, knowledge about specific genetic risks may help to clarify risk processes. Numerous biological and psychological processes have been put forward to explain why and how experiences of maltreatment are converted into antisocial behavior toward others, but there is no conclusive evidence that any of these processes can account for the progression from childhood maltreatment to later criminal violence. Moreover, some youngsters make the progression, but others do not, and researchers have sought to understand why. The search has focused on social experiences that may protect some children, overlooking a potential protective role of genes. Genes are assumed to create vulnerability to disease, but from an evolutionary perspective they are equally likely to protect against environmental insult. Maltreatment studies may benefit from ascertaining genotypes associated with sensitivity to stress, and the known functional properties of MAOA may point toward hypotheses, based on neurotransmitter system development, about how stressful experiences are converted into antisocial behavior toward others in some, but not all, victims of maltreatment.

Although individuals having the combination of low-activity MAOA genotype and maltreatment were only 12% of the male birth cohort, they were 22% of those with multiple antisocial outcomes, yielding an attributable risk fraction (11%) comparable to that of the major risk factors associated with cardiovascular disease. Moreover, 85% of cohort males having a low-activity MAOA genotype who were severely maltreated developed some form of antisocial behavior. Both attributable risk and predictive sensitivity indicate that these findings could inform the development of future pharmacological treatments.

Example 2

Members of the Dunedin Multidisciplinary Health and Development Study were also tested in connection with a hypothesis relating to conditional association between the short allele of Human 5-HTT and depression, where the association is conditioned on experience of stressful life events.

Research sample. Participants were members of the Dunedin Multidisciplinary Health and Development Study. The birth cohort of 1,037 children (52% male) was established at age 3 when the investigators enrolled 91% of the consecutive births between April 1972 and March 1973 in Dunedin, New Zealand. Cohort families represent the full range of socioeconomic status in the general population of New Zealand's South Island. Follow-ups have been carried out at ages 3, 5, 7, 9, 11, 13, 15, 18, 21, and most recently at age 26, when we assessed 96% of the living cohort members. The sample and its history are described in detail elsewhere.

Serotonin transporter genetic variation. We selected to study the 5-HTT gene based on two criteria. (a) Evidence of functionality and (b) evidence that it may moderate response to stress. The promoter activity of the 5-HTT gene, located on 17q11.2, is modified by sequence elements within the proximal 5' regulatory region, designated the serotonin transporter gene-linked polymorphic region (5-HTTLPR). A 20-23 base pair repeat motif within this region occurs as 2 prevalent alleles: One consisting of 14 repeats (the short allele 's') and another of 16 repeats (the long allele 'l'). This polymorphic region has functional significance; 'l/l' homozygote lymphoblast cells produce 1.4-1.7 times the concentration of 5-HTT mRNA than 's/l' and 's/s' cells, uptake of labeled serotonin in 'l/l' homozygote lymphoblast cells is 2 times greater than in 's/l' or 's/s' cells, and the protein produced from 'l/l' cells binds 30-40% more serotonin than cells with the short variant. Although the short promoter variant has not been conclusively linked to depression, experimental paradigms, including studies of 5-HTT knockout mice, stress-reared macaques, and human functional neuroimaging have shown that the 5-HTT gene can interact with environmental conditions to shape reactions to stressful experiences, suggesting to us the hypothesis that variations in the 5-HTT gene may explain why stress leads to depression in some people but not in others.

DNA extraction and genotyping. When the Study members were age 26 years, we obtained DNA from 953 participants (97% of those assessed at that age; 51% male); 93% of the DNA samples were obtained via blood and 7% via buccal swabs for those not wishing to undergo phlebotomy. DNA was extracted from blood samples using standard procedures. A modified procedure was used to extract DNA from buccal cells. Primer sequences for 5-HTTLPR are described by Gelernter et al., the forward primer having the sequence (5'-ATGCCAGCACCTAACCCCTAATGT-3', SEQ ID NO:3) and the reverse (5'-GGACCGCAAGGTGGGCGGGA-3', SEQ ID NO:4). This amplifies a 419 base pair product for the 16 repeat ('l') allele and a 375 base pair product for the 14 repeat ('s') allele. PCR was carried out on a PTC-225 DNA engine (MJ Research), using the following cycling conditions: initial 15-min denaturing step at 95° C., followed by 35 cycles of 94° C. for 30 sec, 66° C. for 30 sec and 72° C. for 40 sec, and a final extension phase of 72° C. for 15 min. Reactions were performed in 10× reaction Buffer IV (ABgene), 1.5 mM $MgCl_2$, 50 ng of genomic DNA, 5 pmols of each primer, 0.3 mM dNTPs and 1 unit of Native Taq (Promega). PCR products were separated on a 2.5% agarose gel (MultiABgarose, ABgene) supplemented with Ethidium bromide (0.03%, BDH) and visualised by ultraviolet transillumination.

Population stratification can probably be ruled out as a confounding factor in this study. First, cohort members reporting Maori ethnicity (7%) were not included in our analysis. Second, a genomic control approach based on latent class analysis was adopted, which suggested that the Caucasian sample was genetically homogeneous. Third, allele frequencies among the non-Maori members of our study were consistent with previously reported allele frequencies in Caucasian populations: 57% for the 16 repeat ('l') allele and 43% for the 14 repeat ('s') allele. No other alleles were detected.

We followed the well-documented functional classification described by Lesch et al. The sample was split into three groups on the basis of genotype, s/s (N=147, 17% of sample, 51% male), s/l (N=435, 51% of sample, 51% male) and l/l (N=265, 31% of sample, 51% male). The three groups were in Hardy-Weinberg equilibrium ($\chi^2(2)$=1.91, p=0.41), and there was no significant difference in genotype frequencies between the sexes ($\chi^2(2)$=0.02, p=0.99).

Stressful life events were assessed at age 26 with the aid of a life history calendar, a highly-reliable method for ascertaining life-event histories. The 5-year reporting period covered events occurring after the $21^{st}$ birthday and before the $26^{th}$ birthday. Events included employment problems (long-term unemployment; being made redundant; losing a job because the company moved; being fired); financial problems (problems with debt, such as having items repossessed; not having enough money to pay for food or household expenses; lacking money for medical expenses; difficulty paying bills); housing problems (homelessness; multiple residential changes); health problems (a disabling physical illness lasting a month or more; a disabling injury); and relationship problems (being involved in a physically violent relationship; a break-up of a cohabiting, intimate relationship). To ensure that the collection of information on life events was not influenced by knowledge of psychiatric outcomes, this information was gathered from Study members by a different interviewer in a separate session. 30% of the Study members experienced no stressful life events, 25% experienced 1 event, 20% 2 events, 11% 3 events, and 15% 4 or more events. Males experienced more stressful life events than females, $X^2(4)$=10.6, p=0.03. There were no significant differences between the three genotype groups in the number of life events they experienced, F(2,846)=0.56, P=0.59, suggesting that 5-HTTLPR genotype did not influence exposure to stressful life events in adulthood.

Childhood maltreatment. To assess children's experience of stressful life events, we measured their experience of maltreatment between ages 3 to 11 years, as previously described by Caspi et al. Evidence of childhood maltreatment was ascertained using behavioral observations, parental reports, and retrospective reports by the Study members. First, mother-child interactions were observed during the child's age-3 assessment. The mother was rated by an observer on eight categories: mother's affect toward the child was consistently negative; harshness toward the child; rough, awkward handling of the child; no effort to help child; unaware or unresponsive to child's needs; indifferent to child's performance; demanding of child's attention; soiled, unkempt appearance of child. Mothers engaging in 2 or more such behaviors were classified as rejecting. Second, harsh discipline was measured at ages 7 and 9 using a checklist on which parents indicated if they engaged in ten disciplinary behaviors such as "smack him or hit him with something." Parents scoring in the top decile of the sample-wide distribution were classified as unusually harsh, relative to the culture in which this cohort grew up. Third, changes in the person occupying the role of the child's primary caregiver were ascertained at each assessment. Children who experienced 2 or more such changes during the first decade of life were classified as having suffered disruptive caregiver changes. Fourth, exposure to child physical abuse was assessed retrospectively at age 26 as part of an interview about victimization. Study members were classified as physically abused if they reported multiple episodes of severe physical punishment (e.g., strapping leaving welts; whipping with electric cords) resulting in lasting bruising or injury before age 11. Fifth, unwanted sexual contact was assessed retrospectively at age 26 as part of an interview about reproductive health. Study members were classified as sexually abused if they reported having their genitals touched, touching another's genitals, or attempted/completed sexual intercourse before age 11. We derived a cumulative exposure index for each child by counting the number of maltreatment experiences during the first decade of life; in the full sample, 64% of the children experienced no maltreatment, 27% experienced 1 indicator of maltreatment, and 9% experienced 2 or more indicators of maltreatment. There was no significant association between the three genotype groups and maltreatment ($X^2(4)$=1.67, p=0.80), suggesting that 5-HTTLPR genotype did not influence exposure to maltreatment in childhood.

Depression outcomes at age 26. Depression was assessed at age 26 using the Diagnostic Interview Schedule, administered by clinicians with a medical or clinical psychology degree. The reporting period was 12 months prior to interview, which occurred within 60 days of the $26^{th}$ birthday. This structured interview yields a continuous measure of depressive symptoms (M=5.2, SD=10.5; Cronbach's alpha=0.95) as well as a diagnosis of a major depressive episode according to DSM-IV criteria. The essential feature of a major depressive episode is a period of at least two weeks during which there is either depressed mood or the loss of interest or pleasure in all activities. One must also experience four of the following additional symptoms: changes in weight or appetite, sleep, or psychomotor activity; decreased energy; feelings of worthlessness or guilt; difficulty thinking or concentrating; or recurrent thoughts of death or suicidal ideation. Lastly, the episode must be accompanied by clinically significant distress or impairment in social, occupational or other important areas of functioning. 17% of Study members (58% female vs. 42% male; OR=1.6, 95% CI: 1.1-2.2) met criteria for a past-year major depressive episode, which is comparable to age and sex prevalence rates observed in U.S. epidemiological studies. In addition to analyzing the diagnostic outcome of depression, we also examined specific evidence of suicide ideation/attempt; 3% of the Study members reported suicide attempts or recurrent thoughts about suicide in the context of a depressive episode. We also collected informant reports about symptoms of depression for 96% of Study members at age 26, by mailing a brief questionnaire to persons nominated by each Study member as "someone who knows you well." Informants were best friends, partners, or other family members. Using a 3-point scale (0=no, doesn't apply; 1=applies somewhat; 2=certainly applies), informants rated the Study member on 4 different symptoms: "feels depressed, miserable, sad, or unhappy," "feels that no one loves them," "seems lonely," and "talks about suicide" (M=1.0; SD=1.2; Cronbach's alpha=0.80).

Measures of depression at ages 18 and 21. Depression symptoms and diagnoses were derived in the same way at ages 18 and 21 as at age 26 (described above). Study members were interviewed with the Diagnostic Interview Schedule at ages 18 and 21 years. At those assessments, the interviews covered the 12-month periods prior to the $18^{th}$ (age 17 years) and $21^{st}$ (age 20 years) birthdays.

Statistical analysis. We used a moderated regression framework to estimate the association between depression and (a) 5-HTTLPR genotype, (b) stressful life events, and (c) their interaction. Sex was entered into the regressions as a covariate. The equation for the models is as follows Depression=$b0+b1$(Sex)+$b2$(5-HTTLPR)+$b3$(Stress)+ $b4$(5-HTTLPR*Stress), where $b0$ is the intercept, $b1$ is the regression coefficient associated with the effect of sex, which is coded as:

0=female; 1=male, $b2$ is the regression coefficient associated with the effect of variations in the serotonin transporter gene promoter, which is here coded to reflect the number of long ('l') alleles, such that:

0=ss; 1=sl; 2=ll, $b3$ is the coefficient associated with the effect of stressful life events, coded to reflect the number of life events, such that:

0=no stressful events;
1=1 stressful event;
2=2 stressful events;
3=3 stressful events;
4=4+ stressful events, $b4$ is the coefficient associated with the interaction effect, which is the product of the two variables (5-HTTLPR and Stressful Life Events). For continuous measures (self-reports and informant reports of depression symptoms), we used ordinary least squares (OLS) regression; for categorical measures (diagnosis of major depression and suicide ideation/attempt), we used logistic regression.

The full results of these regression analyses are provided in Tables 3 through 5. The coefficients (labeled as b) in Tables 3-7 are the model parameters for each type of model (e.g., OLS, logistic) before any transformation (e.g., exponentiation to obtains odds ratios). Predicted values can be plotted using variable values.

In additional analyses we examined the moderating effect of 5-HTTLPR on the association between stress and depression, as a function of MAOA genotype. Genotyping details about MAOA are provided in Caspi et al. Study members were grouped as "low" MAOA activity (carrying the 2, 3 or 5 repeat variants; 61% male) and "high" MAOA activity (carrying the 3.5 or 4 repeat variants; 75% male). As the gene is situated on the X chromosome, only females are heterozygous (23% of the sample). We observed that the influence of life stress on depression was moderated by variation in the 5-HTT gene, regardless of individuals' MAOA genotype. Among carriers of an 's' allele, the effect of stressful life events on depression was consistently significant, whether they had low- or high-MAOA activity status (Table 6). In contrast, among l/l homozygotes, the effect of stressful life events on depression was nonsignificant, regardless of MAOA status (Table 7).

Assessing the robustness of the G×E effect. We incorporated five analytic features into this study to test the robustness of the G×E effect. First, we tested that the G×E interaction on depression obtained whether stress occurred in childhood or in adulthood. Second, we tested that the G×E interaction predicted within-individual increases in depression from a baseline measured before life events occurred. Third, we tested that the G×E interaction was not an artefact of genetic vulnerability evoking life events. Fourth, we used informant reports of depression to rule out the possibility of self-report biases. Fifth, we examined multiple outcome measures, which is of particular importance in the behavioral sciences because different measurements have different sources of error associated with them. Conducting multiple tests is problematic in the following situation: when (a) several tests are conducted, (b) only a small subset of the tests attain significance, and (c) the small number that attain significance can be explained by chance. This situation is even more problematic if (d) no hypothesis was stated in advance, or (e) researchers selectively report only the test that attained significance. In contrast, as in the present study, multiple statistical tests can provide evidence that a finding is robust in the following situation: (a) several tests are conducted using different methods of measurement and analysis, (b) all findings are in the same direction and all of the tests attain significance (or very near-significance), and (c) this number of significant tests exceeds the proportion that could be explained by chance. This situation provides even better evidence of a sturdy finding if, as in the present study, (d) a clear hypothesis was stated in advance, and (e) the researchers collect multiple outcome measures and report all of them to document that the finding is not an artefact of one measurement approach.

847 Caucasian non-Maori Study members, without stratification confounds, were divided into three groups on the basis of their 5-HTTLPR genotype: those with two copies of the 's' allele (s/s homozygotes; n=147, 17%), those with one copy of the 's' allele (s/l heterozygotes; n=435, 51%), and those with two copies of the 'l' allele (l/l homozygotes; n=265, 31%). There was no difference in genotype frequencies between the sexes ($\chi^2(2)$=0.02, P=0.99). Stressful life events occurring after the 21$^{st}$ birthday and before the 26$^{th}$ birthday were assessed with the aid of a life history calendar, a highly reliable method for ascertaining life-event histories. The 14 events included employment, financial, housing, health, and relationship stressors. 30% of the Study members experienced no stressful life events, 25% experienced 1 event, 20% 2 events, 11% 3 events, and 15% 4 or more events. There were no significant differences between the three genotype groups in the number of life events they experienced, F(2, 846)=0.56, P=0.59, suggesting that 5-HTTLPR genotype did not influence exposure to stressful life events.

Study members were assessed for past-year depression at age 26 using the Diagnostic Interview Schedule, which yields a quantitative measure of depressive symptoms and a categorical diagnosis of a major depressive episode according to DSM-IV criteria. 17% of Study members (58% female vs. 42% male; Odds Ratio=1.6, 95% CI: 1.1-2.2) met criteria for a past-year major depressive episode, which is comparable to age and sex prevalence rates observed in U.S. epidemiological studies. In addition, 3% of the Study members reported past-year suicide attempts or recurrent thoughts about suicide in the context of a depressive episode. We also collected informant reports about symptoms of depression for 96% of Study members at age 26 by mailing a brief questionnaire to persons nominated by each Study member as "someone who knows you well."

We used a moderated regression framework, with sex as a covariate, to test the association between depression and (a) 5-HTTLPR genotype, (b) stressful life events, and (c) their interaction (Table 3).

symptoms over time among individuals with an 's' allele, by statistically controlling for the baseline number of depressive symptoms they had before the life events occurred (Table 3). The significant interaction (P=0.05) showed that individuals carrying an 's' allele whose life events occurred after their 21$^{st}$ birthday experienced increases in depressive symptoms from age 21 to 26 years (b=1.55, SE=0.66, t=2.35, P=0.02 among s/s homozygotes, and b=1.25, SE=0.34, t=3.66, P<0.001 among s/l heterozygotes) whereas l/l homozygotes did not (b=0.17, SE=0.41, t=0.41, P=0.68).

Figure 3:
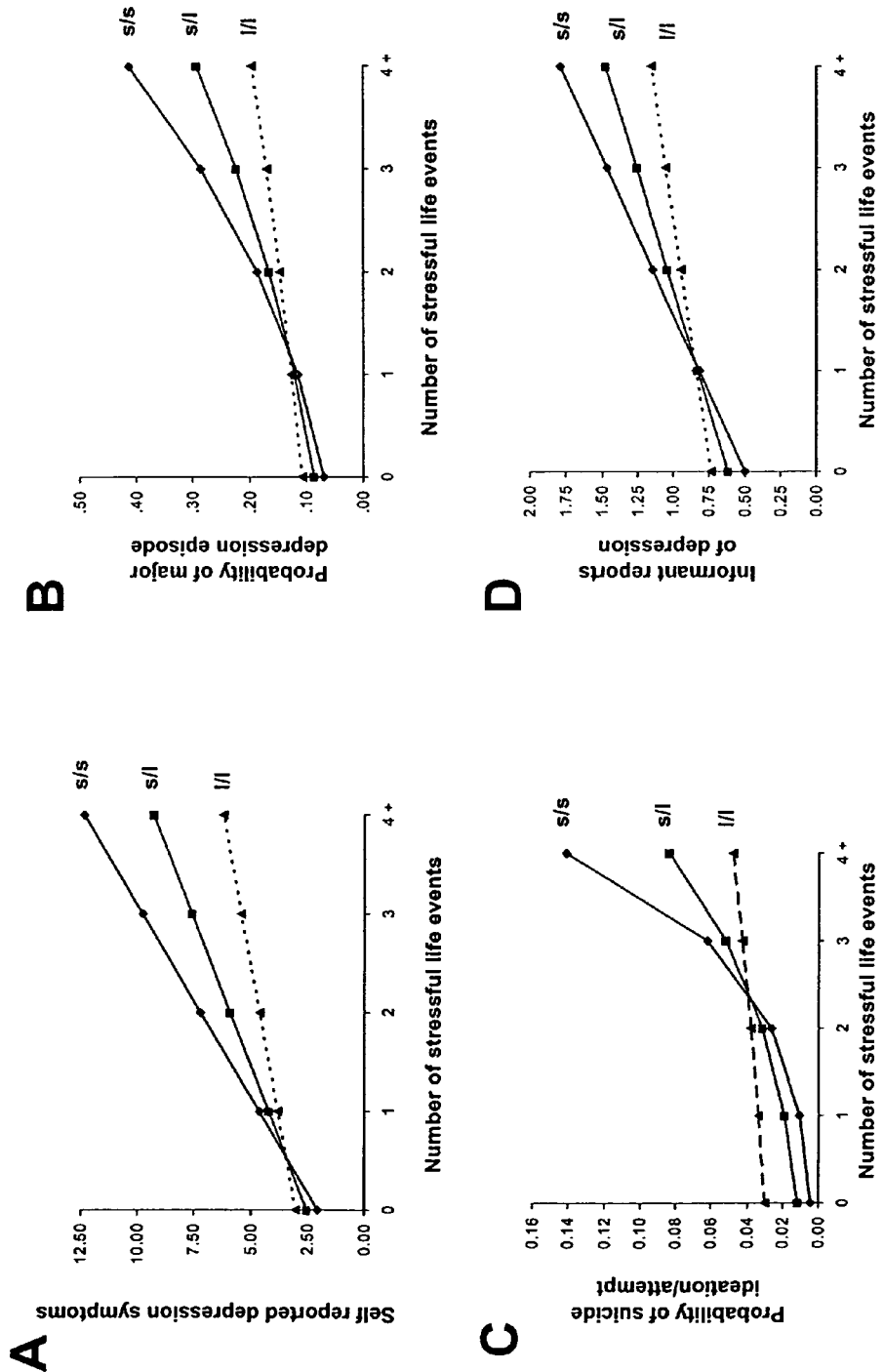
FIG. 3 depicts results of multiple regression analyses estimating the association between number of stressful life events (between ages 21-26 years) and depression outcomes at age 26, as a function of 5-HTT genotype. Among the 146 s/s homozygotes, 43 (29%), 37 (25%), 28 (19%), 15 (10%), and 23 (16%) Study members experienced 0, 1, 2, 3, and 4+stressful events, respectively. Among the 435 s/l heterozygotes, 141 (32%), 101 (23%), 76 (17%), 49 (11%), and 68 (16%) experienced 0, 1, 2, 3, and 4+stressful events. Among the 264 l/l homozygotes, 79 (29%), 73 (28%), 57 (21%), 26 (10%), and 29 (11%) experienced 0, 1, 2, 3, and 4+stressful events. (A) Self-reports of depression symptoms. The main effect of 5-HTTLPR (i.e., an effect not conditional on other variables) was marginally significant (b=−0.96, SE=0.52, t=1.86, P=0.06), the main effect of stressful life events was significant (b=1.75, SE=0.23, t=7.45, P<0.001), and the interaction between 5-HTTLPR and life events was in the predicted direction (b=−0.89, SE=0.37, t=2.39, P=0.02). The interaction showed that the effect of life events on self-reports of depression symptoms was stronger among individuals carrying an 's' allele (b=2.52, SE=0.66, t=3.82, P<0.001 among s/s homozygotes, and b=1.71, SE=0.34, t=5.02, P<0.001 among s/l heterozygotes) than among l/l homozygotes (b=0.77, SE=0.43, t=1.79, P=0.08). (B) Probability of major depressive episode. The main effect of 5-HTTLPR was not significant (b=−0.15, SE=0.14, z=1.07, P=0.29), the main effect of life events was significant (b=0.37, SE=0.06, z=5.99, P<0.001), and the G×E was in the predicted direction (b=−0.19, SE=0.10, z=1.91, P=0.056). Life events predicted a diagnosis of major depression among 's' carriers (b=0.52, SE=0.16, z=3.28, P=0.001 among s/s homozygotes, and b=0.39, SE=0.09, z=4.24, P<0.001 among s/l heterozygotes) but not among l/l homozygotes (b=0.16, SE=0.13, z=1.18, P=0.24). (C) Probability of suicide ideation/attempt. The main effect of 5-HTTLPR was not significant (b=−0.01, SE=0.28, z=0.01, P=0.99), the main effect of life events was significant (b=0.51, SE=0.13, z=3.96, P<0.001), and the G×E interaction was in the predicted direction (b=−0.39, SE=0.20, t=1.95, P=0.051). Life events predicted suicide ideation/attempt among 's' carriers (b=0.48, SE=0.29, z=1.67, P=0.09 among s/s homozygotes, and b=0.91, SE=0.25, z=3.58, P<0.001 among s/l heterozygotes) but not among l/l homozygotes (b=0.13, SE=0.26, z=0.49, P=0.62). (D) Informant reports of depression. The main effect of 5-HTTLPR was not significant (b=−0.06, SE=0.06, t=0.98, P=0.33), the main effect of life events was significant (b=0.23, SE=0.03, t=8.47, P<0.001), and the G×E was in the predicted direction (b=−0.11, SE=0.04, t=2.54, P<0.01). The effect of life events on depression was stronger among 's' carriers (b=0.39, SE=0.07, t=5.23, P<0.001 among s/s homozygotes, and b=0.17, SE=0.04, t=4.51, P<0.001 among s/l heterozygotes) than among l/l homozygotes (b=0.14, SE=0.05, t=2.69, P<0.01).

The G×E interaction also showed that stressful life events predicted a diagnosis of major depression among carriers of an 's' allele, but not among l/l homozygotes (P=0.056, FIG. 3B). We further tested whether life events could predict the onset of new diagnosed depression among carriers of an 's' allele (Table 3). We excluded from analysis Study members who were diagnosed with depression prior to age 21. The significant interaction (P=0.02) showed that life events occurring after their 21$^{st}$ birthdays predicted depression at age 26 among carriers of an 's' allele who did not have a prior history of depression (b=0.79, SE=0.25, z=3.16, P=0.002 among s/s homozygotes, and b=0.41, SE=0.12, z=3.29, P=0.001 among s/l heterozygotes), but did not predict onset of new depression among l/l homozygotes (b=0.08, SE=0.20, z=0.42, P=0.67). Further analyses showed that stressful life events predicted suicide ideation/attempt among individuals carrying an 's'

TABLE 3

Results of final regression analyses testing G × E interaction effects on indices of depression at age 26. The Table presents final models with main effects and interactions entered simultaneously. For continuous measures (self-reports and informant reports of depression symptoms), we used ordinary least squares (OLS) regression; for categorical measures (diagnosis of major depressive episode [MDE] and suicide ideation/attempt), we used logistic regression (see Statistical Analysis section for details).

| Depression outcomes at age 26 | Intercept | Sex | | | | 5-HTTLPR | | | | Life events, ages 21-26 | | | | 5-HTTLPR × Life events | | | |
|---|---|---|---|---|---|---|---|---|---|---|---|---|---|---|---|---|---|
| | | b | se | t/z | p | b | se | t/z | p | b | se | t/z | p | b | se | t/z | p |
| Self-report of depressive symptoms | 3.32 | −2.44 | 0.69 | 3.53 | 0.001 | 0.49 | 0.75 | 0.65 | 0.52 | 2.57 | 0.48 | 5.39 | 0.001 | −0.89 | 0.37 | 2.39 | 0.02 |
| Increase in self-report of depressive symptoms* | 3.69 | −1.12 | 0.67 | 1.67 | 0.100 | 0.44 | 0.72 | 0.62 | 0.54 | 1.80 | 0.47 | 3.84 | 0.001 | −0.71 | 0.36 | 1.97 | 0.05 |
| Diagnosis of MDE | −2.29 | −0.62 | 0.20 | 3.11 | 0.002 | 0.25 | 0.24 | 1.03 | 0.30 | 0.56 | 0.13 | 4.35 | 0.001 | −0.19 | 0.10 | 1.91 | 0.056 |
| First diagnosis of MDE† | −2.93 | −0.84 | 0.27 | 3.08 | 0.002 | 0.53 | 0.33 | 1.61 | 0.11 | 0.77 | 0.19 | 4.11 | 0.001 | −0.34 | 0.15 | 2.37 | 0.02 |
| Suicide ideation/attempt | −5.42 | −0.07 | 0.38 | 0.17 | 0.870 | 0.98 | 0.58 | 1.71 | 0.09 | 0.91 | 0.28 | 3.22 | 0.001 | −0.39 | 0.20 | 1.95 | 0.05 |
| Informant report of depressive symptoms | 0.61 | −0.22 | 0.08 | 2.73 | 0.006 | 0.12 | 0.09 | 1.38 | 0.17 | 0.32 | 0.06 | 5.84 | 0.001 | −0.11 | 0.04 | 2.54 | 0.01 |

*This regression equation contains an additional covariate which controls for self-reports of depression symptoms collected during diagnostic interviews with the Study members at ages 18 and 21 years. The model thus tests whether the 5-HTTLPR × Life events interaction predicts within-individual increases in depression symptoms over time.
†This regression equation excludes from analysis Study members who met diagnostic criteria for depression prior to age 21 (27%). The model thus tests whether the 5-HTTLPR × Life events interaction predicts new cases of depression at age 26 years.

The interaction between 5-HTTLPR and life events showed that the effect of life events on self-reports of depression symptoms at age 26 was significantly stronger (P=0.02) among individuals carrying an 's' allele than among l/l homozygotes (FIG. 3A). We further tested whether life events could predict within-individual increases in depression allele, but not among l/l homozygotes (P=0.05, FIG. 3C). The hypothesized G×E interaction was also significant when we predicted informant-reports of age-26 depression (P<0.01); an analysis that ruled out the possibility of self-report bias (FIG. 3D). The interaction showed that the effect of life events on informant reports of depression was stronger among individuals carrying an 's' allele than among l/l homozygotes.

These analyses attest that the 5-HTT gene interacts with life events to predict depression symptoms, an increase in symptoms, depression diagnoses, new-onset diagnoses, suicidality, and an informant's report of depressed behavior.

This evidence that 5-HTTLPR variation moderates the effect of life events on depression does not constitute unambiguous evidence of a G×E interaction because exposure to life events may be influenced by genetic factors; if individuals have a heritable tendency to enter situations where they encounter stressful life events, these events may simply be a genetically-saturated marker. Thus, what we have identified as a Gene×Environment interaction predicting depression could actually reflect a Gene×"Gene" interaction between the 5-HTTLPR and other genes we did not measure. We reasoned that if our measure of life events represents merely genetic risk, then life events would interact with 5-HTTLPR even if they occurred after the depression episode. However, if our measure of life events represents environmental stress, then the timing of life events relative to depression must follow cause-effect order and life events that occur after depression should not interact with 5-HTTLPR to postdict depression. We tested this hypothesis by substituting the age-26 measure of depression with depression assessed in this longitudinal study when Study members were 21 and 18 years old, prior to the occurrence of the measured life events between ages 21-26 years. Whereas the 5-HTTLPR×life events interaction predicted depression at age 26 years, this same interaction did not postdict depression reported at age 21 nor at age 18 years (Table 4), indicating our finding is a true G×E interaction.

Figure 4:
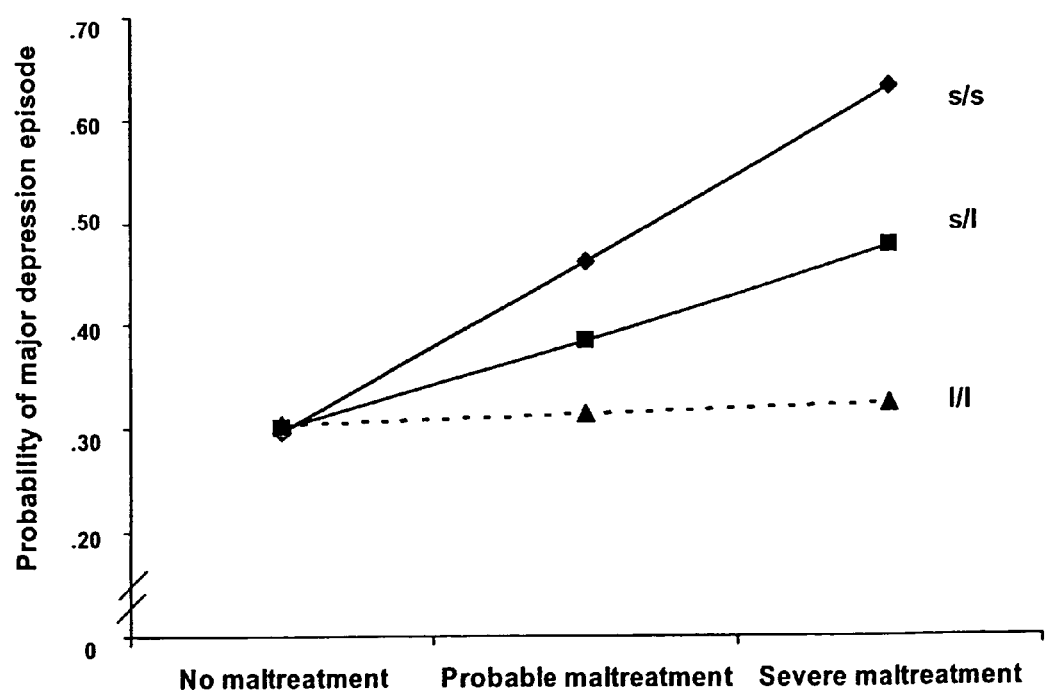
FIG. 4 depicts results of regression analysis estimating the association between childhood maltreatment (between ages 3 to 11 years) and adult depression (ages 18-26), as a function of 5-HTT genotype. Among the 147 s/s homozygotes, 92 (63%), 39 (27%), and 16 (11%) Study members were in the no maltreatment, probable maltreatment, and severe maltreatment groups, respectively. Among the 435 s/l heterozygotes, 286 (66%), 116 (27%), and 33 (8%) were in the no, probable, and severe maltreatment groups. Among the 265 l/l homozygotes, 172 (65%), 69 (26%), and 24 (9%) were in the no, probable, and severe maltreatment groups. The main effect of 5-HTTLPR was not significant (b=−0.14, SE=0.11, z=1.33, P=0.19), the main effect of childhood maltreatment was significant (b=0.30, SE=0.10, z=3.04, P=0.002), and the G×E interaction was in the predicted direction (b=−0.33, SE=0.16, z=2.01, P=0.05). The interaction showed that childhood stress predicted adult depression only among individuals carrying an 's' allele (b=0.60, SE=0.26, z=2.31, P=0.02 among s/s homozygotes, and b=0.45, SE=0.16, z=2.83, P=0.01 among s/l heterozyotes), but not among l/l homozygotes (b=−0.01, SE=0.21, z=0.01, P=0.99).

If 5-HTT genotype moderates the depressogenic influence of stressful life events, it should moderate the effect of life events that occurred not just in adulthood, but also of stressful experiences that occurred in earlier developmental periods. Based on this hypothesis, we tested whether adult depression was predicted by the interaction between 5-HTTLPR and childhood maltreatment that occurred during the first decade of life. Consistent with the G×E hypothesis, the longitudinal prediction from childhood maltreatment to adult depression was significantly moderated by 5-HTTLPR (Table 5). The interaction showed (P=0.05) that childhood maltreatment predicted adult depression only among individuals carrying an 's' allele, but not among l/l homozygotes (FIG. 4).

We previously showed that variations in the gene encoding the neurotransmitter-metabolizing enzyme monoamine oxidase A (MAOA) moderate children's sensitivity to maltreatment. MAOA has high affinity for 5-HT, raising the possibility that the protective effect of the l/l allele on psychiatric morbidity is further augmented by the presence of a genotype conferring high MAOA activity. However, we found that the moderation of life stress on depression was specific to a polymorphism in the 5-HTT gene, as this effect was observed regardless of individuals' MAOA gene status (Tables 6, 7).

TABLE 4

Results of final regression analyses testing G × E interaction effects on depressive symptoms at age 26 years, and on depressive symptoms at the age-21 and age-18 assessments. The Table presents final models with main effects and interactions entered simultaneously. The G × E interaction predicts depression occurring after life events (row 1), but not depression that occurred before life events (rows 2 and 3).

| Self-reports of depression symptoms | Intercept | Sex | | | | 5-HTTLPR | | | | Life events, ages 21-26 | | | | 5HTTLPR × Life events | | | |
|---|---|---|---|---|---|---|---|---|---|---|---|---|---|---|---|---|---|
| | | b | se | t | p | b | se | t | p | b | se | t | p | b | se | t | p |
| Depression symptoms, age 26 | 3.32 | −2.44 | 0.69 | 3.53 | 0.001 | 0.49 | 0.75 | 0.65 | 0.52 | 2.57 | 0.48 | 5.39 | 0.001 | −0.89 | 0.37 | 2.39 | 0.02 |
| Depression symptoms, age 21 | 6.39 | −2.69 | 0.76 | 3.53 | 0.001 | −0.07 | 0.83 | −0.09 | 0.93 | 2.18 | 0.53 | 4.09 | 0.001 | −0.53 | 0.41 | 1.29 | 0.20 |
| Depression symptoms, age 18 | 5.56 | −4.20 | 0.70 | 6.01 | 0.001 | 0.30 | 0.76 | 0.40 | 0.69 | 1.67 | 0.49 | 3.40 | 0.001 | −0.17 | 0.38 | 0.44 | 0.66 |

TABLE 5

Results of final regression analyses testing G × E interaction effects on indices of depression. The Table presents final models with main effects and interactions entered simultaneously. The first row shows the analysis predicting diagnosis of major depressive episode (MDE) at age 26 years; for this analysis, we used logistic regression. The second row shows a supplementary analysis, predicting the number of depression episodes experienced by Study members (range 0-3, as assessed according to independent psychiatric interviews carried out when the Study members were aged 18, 21, and 26 years old); for this analysis, we used a negative binomial regression. Childhood stressful events was treated as a single quantitative variable in the regression analyses, ranging from no maltreatment (=0), to probable maltreatment (=1), to severe maltreatment (=2).

| Depression outcomes | Intercept | Sex | | | | 5HTT | | | | Childhood stressful events, ages 3-11 | | | | 5HTT × Childhood events | | | |
|---|---|---|---|---|---|---|---|---|---|---|---|---|---|---|---|---|---|
| | | b | se | z | p | b | se | Z | p | b | se | z | p | b | se | z | p |
| Any MDE, (ages 18-26) | −0.39 | −0.91 | 0.15 | 6.02 | 0.001 | 0.02 | 0.13 | 0.12 | 0.90 | 0.70 | 0.21 | 3.27 | 0.001 | −0.33 | 0.16 | 2.01 | 0.05 |

TABLE 5-continued

Results of final regression analyses testing G × E interaction effects on indices of depression. The Table presents final models with main effects and interactions entered simultaneously. The first row shows the analysis predicting diagnosis of major depressive episode (MDE) at age 26 years; for this analysis, we used logistic regression. The second row shows a supplementary analysis, predicting the number of depression episodes experienced by Study members (range 0-3, as assessed according to independent psychiatric interviews carried out when the Study members were aged 18, 21, and 26 years old); for this analysis, we used a negative binomial regression. Childhood stressful events was treated as a single quantitative variable in the regression analyses, ranging from no maltreatment (=0), to probable maltreatment (=1), to severe maltreatment (=2).

| Depression outcomes | Intercept | Sex | | | | 5HTT | | | | Childhood stressful events, ages 3-11 | | | | 5HTT × Childhood events | | | |
|---|---|---|---|---|---|---|---|---|---|---|---|---|---|---|---|---|---|
| | | b | se | z | p | b | se | Z | p | b | se | z | p | b | se | z | p |
| Number of age periods with MDE diagnosis (ages 18, 21, 26) | −0.72 | −0.54 | 0.11 | 5.01 | 0.001 | 0.05 | 0.10 | 0.51 | 0.61 | 0.51 | 0.13 | 3.87 | 0.001 | −0.22 | 0.10 | 2.10 | 0.04 |

TABLE 6

The association between stressful life experiences and depression among individuals with either one or two copies of the 5-HTTLPR 's' allele, as a function of MAOA genotype. We used logistic regression analyses to examine the association between young-adult stress and major depression episode at age 26 years, and negative binomial regression analyses to examine the association between childhood stress and number of adult depression episodes between ages 18-26. Sex was a covariate in analyses carried out among the low- and high-MAOA activity groups, but not among the intermediate-MAOA activity group, as the MAOA gene is situated on the X chromosome and only females are heterozygous. Individuals with a 5-HTTLPR 's' allele

| | MAOA genotype | | | | | | | | | | | |
|---|---|---|---|---|---|---|---|---|---|---|---|---|
| | Low-MAOA activity genotype (n = 141) | | | | Intermediate-MAOA activity genotype (n = 134) | | | | High-MAOA activity genotype (n = 300) | | | |
| | b | SE | z | p | b | SE | z | p | b | SE | z | p |
| Young-adult stress ---> depression at age 26 | .67 | .17 | 3.98 | .001 | .43 | .17 | 2.56 | .01 | .33 | .11 | 3.00 | .003 |
| Childhood stress ---> adult depression | .40 | .16 | 2.57 | .01 | .33 | .18 | 1.84 | .07 | .40 | .12 | 3.25 | .001 |

TABLE 7

The association between stressful life experiences and depression among individuals homozygous for the 5-HTTLPR 'l' allele, as a function of MAOA genotype. See Table S4 for details.
Individuals homozygous for the 5-HTTLPR 'l' allele

| | MAOA genotype | | | | | | | | | | | |
|---|---|---|---|---|---|---|---|---|---|---|---|---|
| | Low-MAOA activity genotype (n = 62) | | | | Intermediate-MAOA activity genotype (n = 57) | | | | High-MAOA activity genotype (n = 140) | | | |
| | b | SE | z | p | b | SE | z | p | b | SE | z | p |
| Young-adult stress ---> depression at age 26 | −.03 | .32 | .10 | .92 | .21 | .24 | .87 | .39 | .17 | .21 | .84 | .40 |

TABLE 7-continued

The association between stressful life experiences and
depression among individuals homozygous for the
5-HTTLPR 'l' allele, as a function of MAOA
genotype. See Table S4 for details.
Individuals homozygous for the 5-HTTLPR 'l' allele

| | MAOA genotype | | | | | | | | | | | |
|---|---|---|---|---|---|---|---|---|---|---|---|---|
| | Low-MAOA activity genotype (n = 62) | | | | Intermediate-MAOA activity genotype (n = 57) | | | | High-MAOA activity genotype (n = 140) | | | |
| | b | SE | z | p | b | SE | z | p | b | SE | z | p |
| Childhood stress ---> adult depression | .06 | .30 | .21 | .84 | .02 | .27 | .07 | .94 | −.08 | .27 | .32 | .75 |

Figure 5:
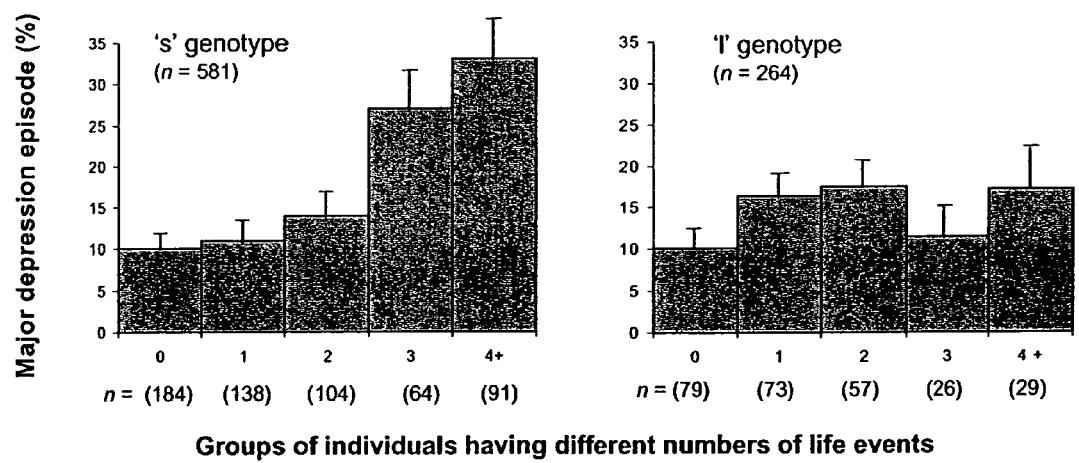
FIG. 5 depicts the percentage of individuals meeting diagnostic criteria for depression at age 26, as a function of 5-HTT genotype and number of stressful life events between ages 21-26. The figure shows individuals with either one or two copies of the short allele ('s' group) and individuals homozygous for the long allele ('l' group). In a hierarchical logistic regression model, the main effect of genotype (coded as 's' group=0, 'l' group=1) was not significant, b=−0.15, SE=0.21, z=0.72, P=0.47, the main effect of number of life events was significant, b=0.34, SE=0.06, z=5.70, P<0.001, and the interaction between genotype and number of life events was significant, b=−0.30, SE=0.15, z=1.97, P=0.05.

Although carriers of an 's' 5-HTTLPR allele who experienced 4 or more life events constituted only 10% of the birth cohort, they accounted for almost one-quarter (23%) of the 133 cases of diagnosed depression. Moreover, among cohort members suffering 4 or more life events, 33% of individuals with an 's' allele became depressed, whereas only 1.7% of the l/l homozygotes developed depression (FIG. 5). Thus, the G×E's attributable risk and predictive sensitivity indicate that more knowledge about the functional properties of the 5-HTT gene may lead to better pharmacological treatments for those already depressed. Although the short 5-HTTLPR variant is too prevalent for discriminatory screening (over half of the Caucasian population has an 's' allele), a microarray of genes might eventually identify those needing prophylaxis against life's stressful events.

Evidence of a direct relation between the 5-HTTLPR and depression has been inconsistent, perhaps because prior studies have not considered participants' stress histories. In this study, no direct association between the 5-HTT gene and depression was observed. Previous experimental paradigms including 5-HTT knockout mice, stress-reared rhesus macaques, and human functional neuroimaging have shown that the 5-HTT gene can interact with environmental conditions, although these experiments did not address depression. Our study demonstrates that this G×E interaction extends to the natural development of depression in a representative sample of humans. However, we could not test hypotheses about brain endophenotypes intermediate between the 5-HTT gene and depression because of the difficulty of taking CSF or fMRI measures in an epidemiological cohort.

Much genetic research has been guided by the assumption that genes cause diseases, but the expectation that direct paths will be found from gene to disease has not proven fruitful for complex psychiatric disorders. Our findings of G×E interaction for the 5-HTT gene, and another candidate gene MAOA, point to a different, evolutionary model. This model assumes that genetic variants maintained at high prevalence in the population probably act to promote organisms' resistance to environmental pathogens. We extend the concept of environmental pathogens to include traumatic, stressful life experiences, and propose that the effects of genes may be uncovered when such pathogens are measured (in naturalistic studies) or manipulated (in experimental studies). To date, few linkage studies detect genes, many candidate gene studies fail consistent replication, and genes that replicate account for little variation in the phenotype. Our G×E findings have implications for improving research in psychiatric genetics. Incomplete gene penetrance, a major source of error in linkage pedigrees, can be explained if a gene's effects are expressed only among family members exposed to environmental risk. If risk exposure differs between samples, candidate genes may fail replication. If risk exposure differs among participants within a sample, genes may account for little variation in the phenotype. We speculate that some multifactorial disorders, instead of resulting from variations in many genes of small effect, may result from variations in fewer genes whose effects are conditional on exposure to environmental risks.

The present invention is not intended to be limited to the foregoing examples but to encompass all such variations and modifications as fall within the scope of the appended claims.

References, each incorporated by reference as if set forth herein in its entirety L. S. Aiken, S. G. West, *Multiple Regression: Testing and Interpreting Interactions* (Sage, Thousand Oaks, Calif., 1991).
M. De Bellis, *Develop. Psychopathol.* 13, 539 (2001).
A. J. Bennet et al., *Molec. Psychiatry* 7, 188 (2002).
M. E. Berman, R. J. Kavoussi, E. F. Coccaro, in *Handbook of Antisocial Behavior*, D. M. Stoff,
D. Bowtell, *Anal. Biochem.* 162, 463 (1987).
J. Breiling, J. D. Maser, Eds. (Wiley, NY, 1997).
J. D. Bremner, E. Vermetten, *Develop. Psychopathol.* 13, 473 (2001).
H. G. Brunner, M. Nele, X. O. Breakefield, H. H. Ropers, B. A. van Oost, *Science* 262, 5133 (1993).
O. Cases et al., *Science* 268, 1763 (1995).
D. Cicchetti, F. A. Rogosch, *Develop. and Psychopathol.* 13 783 (2001).
P. Cohen, J. Cohen, *Arch. Gen. Psychiatry* 41, 1178 (1984).
J. Deckert et al., *Hum. Mol. Gen.* 8, 621 (1999).
R. M. Denney, H. Koch, I. W. Craig, *Hum. Genet.* 105, 542 (1999).
*Diagnostic and Statistical Manual of Mental Disorders*, 4th edition (American Psychiatric Association, Washington, D.C., 1994).
K. A. Dodge, J. E., Bates, G. S. Pettit, *Science* 250 1678 (1990)
D. M. Fergusson, L. J. Horwood, M. T. Lynskey, *J Child Psychol. Psychiatry.* 33, 1059 (1993).
D. D. Francis, M. J. Meany, *Curr. Opin. Neurobiol.* 9 128 (1999).
B. Freeman et al., *Behav. Genet.* 27, 251 (1997).
D. Glaser, *J Child Psychol. Psychiatry* 41, 97 (2000).
S. M. Grundy, R. Paternak, P. Greenland, S. Smith, V. Fuster, *J. Am. Coll. Cardiol.* 34 1348 (1999).

A. V. S. Hill, *Br. Med. Bull.* 55, 401 (1999).

S. R. Jaffee et al. *Arch. Gen. Psychiatry,* 58 215 (2002).

M. Jeanpierre, *Nucleic. Acids. Res.* 15, 9611 (1987).

J. G. Johnson, P. Cohen, J. Brown, E. Smailes, D. P. Bernstein, *Arch. Gen. Psychiatry* 56, 600 (1999).

A. F. Jorm et al., *Psychiatric Genet.* 10, 87 (2000).

A. F. Jorm, S. Easteal, *Soc. Psychiatry Psychiatr. Epidemiol.* 35, 1 (2000).

M. K. Keiley, T. R. Howe, K. A. Dodge, J. E. Bates, G. S. Pettit, *Develop. Psychopathol.* 13, 891 (2001).

K. S. Kendler, *Arch. Gen. Psychiatry* 58, 1005 (2001).

G. W. Kraemer, M. H. Ebert, D. E. Schmidt, W. T. McKinney, *Neuropsychopharmacology* 2, 175 (1989).

R. F. Krueger, A. Caspi, T. E. Moffitt, *J Pers.* 68, 967 (2000).

E. R. Levy, J. F. Powell, V. J. Buckle, Y. P. Hsu, X. O. Breakefield, I. W. Craig *Genomics* 5, 368 (1989).

S. S. Luthar, D. Cicchetti, B. Becker, *Child Develop.* 71, 543 (2000).

D. Lynam, T. E. Moffitt, M. Stouthamer-Loeber, *J Ab. Psychol.* 102 187 (1993).

S. B. Manuck, J. D. Flory, R. E. Ferrell, J. J. Mann, M. F. Muldoon, *Psychiatry Res.* 95, 9 (2000).

T. E. Moffitt, A. Caspi, M. Rutter, P. A. Silva, *Sex Differences in Antisocial Behavior: Conduct Disorder, Delinquency, and Violence in the Dunedin Longitudinal Study* (Cambridge University Press, 2001).

T. E. Moffitt, A Caspi, H. Harrington, B. J. Milne, *Develop. Psychopathol.* 14, 179 (2002).

V. Morrell, *Science* 260, 1722 (1993).

L. K. Muthen, B. O. Muthen, *M-plus.* (Author, Los Angeles, 1999).

A. Parsian, C. R. Cloninger, *Psychiatric Genet.* 11, 89 (2001).

D. Pine et al., *Arch. Gen. Psychiatry.* 54, 839 (1997).

R. Poulton et al., *Lancet*, in press (2002).

A. Raine, P. Brennan, S. A. Mednick, *Arch. Gen. Psychiatry* 51, 984 (1994).

L. N. Robins, *Psychol. Med.* 8, 611 (1978).

D. C. Rowe, *Biology and Crime* (Roxbury, Los Angeles, 2001).

M. Rutter, H. Giller, A. Hagell, *Antisocial Behavior by Young People* (Cambridge University Press, 1998).

M. Rutter, J. Silberg, *Annu. Rev. Psychology* 53, 463 (2002).

S. Z. Sabol, S. Hu, D. Hamer, *Hum. Genet.* 103, 273 (1998).

A. J. Sameroff, M. Lewis, S. Miller, Eds. *Psychopathology,* (Plenum, N.Y., in press).

J. Samochowiec et al., *Psychiatry Res.* 86, 72 (1999).

G. A., Satten, D. Flanders, Q. Yang, *Am. J. Hum. Genet.* 68 466 (2001).

J. C. Shih, K. Chen, M. J. Ridd. *Annu. Rev. Neurosci.* 22, 197 (1999).

J. C. Shih, R. F. Thompson, *Am. J. Hum. Genet.* 65, 593 (1999).

M. A. Straus, D. B. Sugarman, J. Giles-Sims, *Arch. Pediatr. Adolesc. Med.* 151, 761 (1997).

S. J. Suomi, in *Handbook of Developmental* C. S. Widom, Science 244, 160 (1989).

H. E. Ward et al., *Pharmacol. Biochem. Behav.* 60, 209 (1998).

C. S. Widom, in *Handbook of Antisocial Behavior*, D. M. Stoff, J. Breiling, J. D. Maser, Eds. (Wiley, New York, 1997).

World Health Organization, *Comparative Quantification of Health Risks: Global and Regional Burden of Disease Due to Selected Risk Factors* (WHO, Geneva, in press).

REFERENCES & NOTES

L. S. Aiken, S. G. West, *Multiple Regression: Testing and Interpreting Interactions* (Sage, Thousand Oaks, Calif., 1991).

R. F. Belli, W. L. Shay, F. P. Stafford, *Public Opin. Quart.* 65, 45 (2001).

A. J. Bennett et al., Mol. *Psychiatry* 7, 188 (2002).

D. Bowtell, *Anal. Biochem.* 162, 463 (1987).

G. W. Brown, *Soc. Psychiat., Psychiatric. Epid.* 33, 363 (1998).

A. Caspi et al., *Int. J. Methods Psychiatric Res.* 6, 101 (1996).

A. Caspi et al., *Science* 297, 851 (2002).

E. J. Costello et al., *Biol. Psychiatry* 52, 529 (2002).

*Diagnostic and Statistical Manual of Mental Disorders* (American Psychiatric Association, Washington, D.C., ed. 4, 1994).

W. E. Evans, M. V. Relling, *Science* 286, 487 (1999).

B. Freeman et al., *Behav. Genet.* 33, 67 (2002).

J. Gelemter, H. Kranzler, J. F. Cubells, *Hum. Genet.* 101, 243 (1997).

I. I. Gottesman, T. D. Gould, *Am. J. Psychiatry* 160, 636 (2003).

D. Hamer, *Science* 298, 71 (2002).

A. R. Hariri et al., *Science* 297, 400 (2002).

A. V. S. Hill, *Br. Med. Bull.* 55, 401 (1999).

Institute of Medicine, *Reducing risks for mental disorders* (Washington, D.C., National Academy Press, 1994).

S. R. Jaffee et al. *Arch. Gen. Psychiatry* 58 215 (2002).

M. Jeanpierre, *Nucleic. Acids. Res.* 15, 9611 (1987).

K. S. Kendler et al., *Am. J. Psychiatry* 152, 833 (1995).

K. S. Kendler, L. Karkowski-Shuman, *Psychol. Med.* 27, 539 (1997).

K. S. Kendler, L. M. Karkowski, C. A. Prescott, *Am. J. Psychiatry* 156, 837 (1999).

R. C. Kessler, *Annu. Rev. Psychol,* 48, 191 (1997).

R. C. Kessler, K. A., McGonagle, M. Swartz, D. G. Blazer, C. B. Nelson, *J Affect. Disorders* 29, 85 (1993).

K. P. Lesch, in *Behavioral Genetics in the Postgenomics Era*, R. Plomin, J. C. DeFries, I. W. Craig, P. McGuffin, Eds. (APA, Washington, D.C., 2003), pp. 389-424.

K. P. Lesch, M. D. Greenberg, J. D. Higley, A. Bennett, D. L. Murphy in *Molecular Genetics and the Human Personality*, J. Benjamin, R. P. Ebstein, R. H. Belmaker, Eds. (American Psychiatric Publishing, Washington, D.C., 2002), p. 109-136.

K. P. Lesch et al., *Science* 274, 1527 (1996).

T. E. Moffitt, A. Caspi, M. Rutter, P. A. Silva, *Sex Differences in Antisocial Behavior: Conduct Disorder, Delinquency, and Violence in the Dunedin Longitudinal Study* (Cambridge Univ. Press, Cambridge, 2001).

S. M. Monroe, A. D. Simons, *Psychol. Bull.* 110, 406 (1991).

D. L. Murphy et al., *Brain Res. Bull.* 56, 487 (2001).

D. S. Pine, P. Cohen, J. G. Johnson, J. S. Brook, *J Affect. Disorders* 68, 49 (2002).

R. Plomin, C. S. Bergeman, *Behav. Brain Sci.* 14, 373 (1991).

L. N. Robins, L. Cottler, K. Bucholtz, W. Compton, *Diagnostic Interview Schedule for DSM-IV* (Washington University, St. Louis, Mo., 1995).

N. Salichon et al., *J. Neurosci.* 21, 884 (2001).

G. A. Satten, D. Flanders, Q. Yang, *Am. J. Hum. Genet.* 68 466 (2001).

C. A. Tamminga et al., *Biol. Psychiatry* 52, 589 (2002).

C. J. Tang, A. D. Lopez, *Lancet* 349, 1498 (1997).

Materials and methods are available as supporting material on Science Online.

We claim:

1. A method for detecting one or more copies of a short promoter allele of a 5-HTT gene and diagnosing a predisposition to depression in a human subject who has experienced a stressful life event, the method comprising the steps of:
   a) performing a genotyping assay on a nucleic acid sample of said human subject to detect the presence of one or more copies of the short promoter allele of the 5-HTT gene, and
   b) determining that the human subject is predisposed to depression if the human subject has one or more copies of the short promoter allele of the 5-HTT gene.

2. A method for detecting one or more copies of a short promoter allele of a 5-HTT ene and performing a therapy in a human subject who has experienced a stressful life event, the method comprising the steps of:
   a) performing a genotyping assay on a nucleic acid sample of said human subject to detect the presence of one or more copies of a short promoter allele of the 5-HTT gene,
   b) determining that the human subject is predisposed to depression if the human subject has one or more copies of the short promoter allele of the 5-HTT gene, and
   c) treating the human subject determined in step b) to be predisposed to depression in a manner consistent with predisposition to depression, the manner selected from the group consisting of counseling the subject to pursue or avoid a particular type of employment and prescribing a therapy.

3. The method of claim 1, wherein the genotyping assay comprises amplifying a portion of the 5-HTT gene using an amplification primer pair that distinguishes the short promoter allele from other alleles of the 5-HTT gene; and determining whether the amplified portion is a fragment of the short promoter allele.

4. The method of claim 3, wherein the amplification primer pair comprises a first primer having the sequence of SEQ ID NO: 3 and a second primer having the sequence of SEQ ID NO: 4.

5. The method of claim 2, wherein the therapy is selected from the group consisting of psychological therapy and pharmaceutical therapy.

6. The method of claim 5, wherein the pharmaceutical therapy comprises treatment with an anti-depressive agent.

* * * * *

UNITED STATES PATENT AND TRADEMARK OFFICE
CERTIFICATE OF CORRECTION

| | | |
|---|---|---|
| PATENT NO. | : 7,972,779 B2 | Page 1 of 1 |
| APPLICATION NO. | : 10/889450 | |
| DATED | : July 5, 2011 | |
| INVENTOR(S) | : Avshalom Caspi and Terrie E. Moffitt | |

It is certified that error appears in the above-identified patent and that said Letters Patent is hereby corrected as shown below:

Column 1, line 3, please insert:

-- STATEMENT REGARDING FEDERALLY SPONSORED RESEARCH OR DEVELOPMENT

This invention was made with government support under MH45070 awarded by the National Institutes of Health. The government has certain rights in this invention. --

Signed and Sealed this
Ninth Day of August, 2011

David J. Kappos
*Director of the United States Patent and Trademark Office*